(12) United States Patent
Chang et al.

(10) Patent No.: US 11,864,547 B2
(45) Date of Patent: Jan. 9, 2024

(54) ADHESIVE-TYPE INSECT TRAP HAVING A COVER WITH A LIGHT REFRACTING PORTION FORMED THEREON

(71) Applicant: SEOUL VIOSYS CO., LTD., Gyeonggi-do (KR)

(72) Inventors: Sang Hyun Chang, Gyeonggi-do (KR); Hoon Sik Eom, Gyeonggi-do (KR); Si Ho Yu, Gyeonggi-do (KR); Gwang Ryong Lee, Gyeonggi-do (KR); Chung Hoon Lee, Gyeonggi-do (KR); Sung Il Park, Gyeonggi-do (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 700 days.

(21) Appl. No.: 16/477,149

(22) PCT Filed: Jan. 8, 2018

(86) PCT No.: PCT/KR2018/000344
§ 371 (c)(1),
(2) Date: Jul. 10, 2019

(87) PCT Pub. No.: WO2018/131851
PCT Pub. Date: Jul. 19, 2018

(65) Prior Publication Data
US 2020/0146273 A1 May 14, 2020

(30) Foreign Application Priority Data

Jan. 10, 2017 (KR) .................. 10-2017-0003381
Jun. 9, 2017 (KR) .................. 10-2017-0072801
Sep. 5, 2017 (KR) .................. 10-2017-0113195

(51) Int. Cl.
*A01M 1/04* (2006.01)
*A01M 1/14* (2006.01)
(Continued)

(52) U.S. Cl.
CPC .............. *A01M 1/145* (2013.01); *A01M 1/02* (2013.01); *A01M 1/04* (2013.01); *A01M 1/106* (2013.01);
(Continued)

(58) Field of Classification Search
CPC .......... A01M 1/145; A01M 1/14; A01M 1/04; A01M 1/10; A01M 1/106; A01M 1/16; A01M 1/02
(Continued)

(56) References Cited

U.S. PATENT DOCUMENTS 2,740,216 A * 4/1956 Lieberman .............. F21V 17/04
362/355
3,358,138 A * 12/1967 Trantina ................... F21S 8/02
362/355
(Continued)

FOREIGN PATENT DOCUMENTS

CA          2721590 A1 * 10/2009 ............. A01M 1/02
CN       203087336           7/2013
(Continued)

OTHER PUBLICATIONS

Supplementary European Search Report issued in European Application No. 18738568.7, dated Sep. 11, 2020.
(Continued)

*Primary Examiner* — Darren W Ark
(74) *Attorney, Agent, or Firm* — Perkins Coie LLP

(57) ABSTRACT

An adhesive-type insect trap includes a body having a hole for insertion of an adhesive sheet; a light source mounting unit disposed on the body; and a cover which is detachably mounted on the body and has a through-hole in at least a part thereof, and an adhesive sheet including a sticky substance and a sheet. The body includes a guide unit by which the
(Continued)

adhesive sheet is guided, and the cover comprises a light refraction unit therein or on a surface thereof.

11 Claims, 29 Drawing Sheets

(51) Int. Cl.
 *A01M 1/02* (2006.01)
 *A01M 1/10* (2006.01)
 *A01M 1/16* (2006.01)
 *G01J 1/44* (2006.01)
 *G01V 8/12* (2006.01)

(52) U.S. Cl.
 CPC .............. *A01M 1/14* (2013.01); *A01M 1/165* (2013.01); *G01J 1/44* (2013.01); *G01V 8/12* (2013.01)

(58) Field of Classification Search
 USPC ..................................... 43/114, 113, 115, 107
 See application file for complete search history.

(56) References Cited

U.S. PATENT DOCUMENTS

| | | | | | |
|---|---|---|---|---|---|
| 5,251,397 | A * | 10/1993 | Exum | ............ | A01M 1/145 43/115 |
| 5,513,465 | A * | 5/1996 | Demarest | ............ | A01M 1/145 43/113 |
| 5,950,355 | A * | 9/1999 | Gilbert | ............ | A01M 1/145 43/113 |
| 6,108,965 | A * | 8/2000 | Burrows | ............ | A01M 1/145 43/113 |
| 6,199,315 | B1 * | 3/2001 | Suzue | ............ | A01M 1/14 43/113 |
| 6,393,759 | B1 * | 5/2002 | Brown | ............ | A01M 1/023 43/113 |
| 6,397,515 | B1 * | 6/2002 | Brown | ............ | A01M 1/023 43/113 |
| 6,860,061 | B2 * | 3/2005 | Nosse | ............ | A01M 1/08 43/112 |
| 6,886,292 | B2 * | 5/2005 | Studer | ............ | A01M 1/145 43/112 |
| 7,856,752 | B1 * | 12/2010 | Eilersen | ............ | A01M 1/14 43/115 |
| 8,519,610 | B2 * | 8/2013 | Tsuji | ............ | H01L 51/5275 313/503 |
| 8,739,461 | B2 * | 6/2014 | Studer | ............ | A01M 1/145 43/115 |
| 8,814,410 | B2 * | 8/2014 | McCollum | ............ | G02B 5/045 362/268 |
| 8,870,409 | B2 * | 10/2014 | Ye | ............ | F21K 9/66 362/337 |
| 8,888,333 | B2 * | 11/2014 | Yapel | ............ | G02F 1/133606 362/558 |
| 9,595,648 | B2 * | 3/2017 | Inada | ............ | H01L 51/5275 |
| 10,051,851 | B2 * | 8/2018 | Hariyama | ............ | A01M 1/223 |
| 10,327,435 | B2 * | 6/2019 | Studer | ............ | A01M 1/145 |
| 10,561,135 | B2 * | 2/2020 | Sandford | ............ | F21V 7/28 |
| 10,588,307 | B2 * | 3/2020 | Sandford | ............ | A01M 1/023 |
| 10,675,374 | B2 * | 6/2020 | Kaye | ............ | A61L 9/20 |
| 10,694,733 | B2 * | 6/2020 | Willcox | ............ | A01M 1/145 |
| 10,973,225 | B2 * | 4/2021 | Studer | ............ | A01M 1/106 |
| 11,109,583 | B2 * | 9/2021 | Parnell | ............ | A01M 1/145 |
| 2002/0032980 | A1 | 3/2002 | Nelson | | |
| 2002/0139040 | A1 * | 10/2002 | Burrows | ............ | A01M 1/145 43/113 |
| 2003/0089024 | A1 | 5/2003 | Nelson et al. | | |
| 2004/0189185 | A1 * | 9/2004 | Yotsuya | ............ | H01L 51/5275 313/112 |
| 2006/0107583 | A1 * | 5/2006 | Wu | ............ | A01M 1/04 43/113 |
| 2007/0124987 | A1 * | 6/2007 | Brown | ............ | A01M 1/023 43/113 |
| 2007/0169401 | A1 * | 7/2007 | Chyun | ............ | A01M 1/145 43/107 |
| 2008/0229652 | A1 * | 9/2008 | Willcox | ............ | A01M 1/145 43/113 |
| 2011/0041384 | A1 * | 2/2011 | Willcox | ............ | A01M 1/145 43/113 |
| 2011/0280004 | A1 * | 11/2011 | Shimada | ............ | G02B 5/0221 359/599 |
| 2012/0297662 | A1 * | 11/2012 | Strube | ............ | A01M 1/145 43/113 |
| 2013/0033863 | A1 * | 2/2013 | Gould | ............ | F21V 5/008 362/235 |
| 2014/0026467 | A1 * | 1/2014 | Kaye | ............ | A01M 1/145 43/113 |
| 2014/0131675 | A1 * | 5/2014 | Chien | ............ | H01L 51/5275 362/326 |
| 2015/0146451 | A1 * | 5/2015 | Yuan | ............ | G02B 6/0051 362/330 |
| 2015/0167921 | A1 * | 6/2015 | Gollier | ............ | G02B 5/0226 362/326 |
| 2015/0176797 | A1 * | 6/2015 | Inoue | ............ | F21V 5/002 359/599 |
| 2015/0211709 | A1 * | 7/2015 | Uchida | ............ | F21K 9/60 362/311.09 |
| 2015/0344736 | A1 * | 12/2015 | Shin | ............ | F21K 9/27 524/413 |
| 2016/0025919 | A1 * | 1/2016 | Boyd | ............ | G02B 5/0221 362/330 |
| 2016/0070053 | A1 * | 3/2016 | Hwang | ............ | C08K 9/04 362/330 |
| 2016/0141554 | A1 * | 5/2016 | Hashiya | ............ | G02B 3/0068 362/330 |
| 2017/0258068 | A1 * | 9/2017 | Eom | ............ | A01M 1/106 |
| 2017/0290322 | A1 * | 10/2017 | Soeno | ............ | A01M 1/04 |
| 2017/0295772 | A1 * | 10/2017 | Studer | ............ | A01M 1/145 |
| 2018/0213763 | A1 * | 8/2018 | Lee | ............ | A01M 1/106 |
| 2018/0271080 | A1 * | 9/2018 | Kim | ............ | F21V 23/0464 |
| 2019/0090470 | A1 * | 3/2019 | Lee | ............ | A01M 1/106 |
| 2019/0133106 | A1 * | 5/2019 | Eom | ............ | A01M 1/04 |
| 2019/0141978 | A1 * | 5/2019 | Smith | ............ | A01M 1/023 43/113 |
| 2019/0174736 | A1 * | 6/2019 | Smith | ............ | A01M 1/145 |
| 2019/0261616 | A1 * | 8/2019 | Studer | ............ | A01M 1/145 |
| 2019/0350184 | A1 * | 11/2019 | Chang | ............ | A01M 1/02 |
| 2020/0375168 | A1 * | 12/2020 | Kaye | ............ | A01M 1/106 |
| 2021/0368763 | A1 * | 12/2021 | Fish | ............ | A01M 1/145 |
| 2021/0404646 | A1 * | 12/2021 | Wang | ............ | F21K 9/27 |
| 2022/0022442 | A1 * | 1/2022 | Studer | ............ | A01M 1/04 |
| 2022/0039366 | A1 * | 2/2022 | Parnell | ............ | G09F 9/30 |

FOREIGN PATENT DOCUMENTS

| | | | |
|---|---|---|---|
| CN | 203897100 | 10/2014 | |
| GB | 2373705 A * | 10/2002 | ............ A01M 1/145 |
| GB | 2459717 | 11/2009 | |
| JP | 2009-043635 | 2/2009 | |
| JP | 4256441 | 4/2009 | |
| JP | 2009183164 | 8/2009 | |
| JP | 5216054 | 6/2013 | |
| JP | 2016509843 | 4/2016 | |
| JP | 2019000086 A * | 1/2019 | |
| JP | 2020005582 A * | 1/2020 | |
| JP | 2020064768 A * | 4/2020 | |
| KR | 20080107920 A * | 12/2008 | |
| KR | 1020080107918 | 12/2008 | |
| KR | 2020080006034 | 12/2008 | |
| KR | 100895486 | 5/2009 | |
| KR | 100895489 | 5/2009 | |
| KR | 10-2009-0064070 | 6/2009 | |
| KR | 20090061454 A * | 6/2009 | |
| KR | 100968199 | 7/2010 | |
| KR | 1020100078422 | 7/2010 | |
| KR | 20120029689 A * | 3/2012 | |
| KR | 1020120073476 | 7/2012 | |
| KR | 101200363 B1 * | 11/2012 | |
| KR | 20120139354 A * | 12/2012 | |
| KR | 1020120139354 | 12/2012 | |

(56) References Cited

FOREIGN PATENT DOCUMENTS

| KR | 101266861 | | 5/2013 | |
|---|---|---|---|---|
| KR | 101573714 | | 12/2015 | |
| KR | 2020160001863 | | 6/2016 | |
| KR | 10-2016-0098791 | | 8/2016 | |
| KR | 20160098791 A | * | 8/2016 | |
| KR | 101681743 | | 12/2016 | |
| WO | WO-2012080698 A1 | * | 6/2012 | ............. A01M 1/04 |
| WO | 2016207430 | | 12/2016 | |
| WO | WO-2020167330 A1 | * | 8/2020 | ............ A01M 1/145 |
| WO | WO-2021137920 A1 | * | 7/2021 | ............. A01M 1/04 |

OTHER PUBLICATIONS

Supplementary European Search Report issued in European Application No. 18738947.3, dated Sep. 11, 2020.
Office Action issued in corresponding Chinese Application No. 2018800172042, dated Mar. 3, 2021.
International Search Report for International Application No. PCT/KR2018/000344, dated Apr. 25, 2018.
International Search Report for International Application No. PCT/KR2018/000350, dated Apr. 26, 2018.
International Search Report for International Application No. PCT/KR2018/000268, dated Apr. 24, 2018.
Office Action issued in Indian Application No. 201937032046, dated Jan. 18, 2021.
Office Action issued in corresponding Indonesian Application No. P00201906980, dated Apr. 1, 2021.

* cited by examiner

4000

8000

270

370

470

ADHESIVE-TYPE INSECT TRAP HAVING A COVER WITH A LIGHT REFRACTING PORTION FORMED THEREON

RELATED APPLICATIONS

The present application is a U.S. national stage application under 35 U.S.C. § 371 of PCT Application No. PCT/KR2018/000344 filed Jan. 8, 2018, which claims priority to Korean Application Nos. 10-2017-0003381 filed Jan. 10, 2017, 10-2017-0072801 filed Jun. 9, 2017, and 10-2017-0113195 filed Sep. 5, 2017, all of which are hereby incorporated in their entirety by reference as set forth herein.

TECHNICAL FIELD

The present disclosure relates to an adhesive-type insect trap and, more particularly, to an adhesive-type insect trap adapted to collect insects by luring the insects using a light source and attaching the enticed insects thereto. The present disclosure further relates to an adhesive-type insect trap having a cover with a light refracting portion formed thereon.

RELATED ART

Generally, flying insects such as flies, mosquitoes, and moths are infectious vectors that carry various kinds of germs, and cause direct or indirect damage to humans or crops.

Although various pesticides and insecticides have been used to eliminate such harmful insects, such pesticides and insecticides are harmful to a human body and cause ecological imbalance. As an alternative, various methods, such as development of biodegradable insecticides, use of natural enemies or pheromones, and application of insecticide after attraction of insects, have been studied.

As an example of application of insecticide after attraction of insects, there is a so-called electric insecticidal apparatus in which an infrared (IR) heater lamp is mounted inside a main body of the apparatus in order to attract insects exhibiting positive phototaxis to move from the periphery to bright light such that insects attracted to the heater lamp side are electrically charged by heat from the heater lamp. However, due to use of high voltage, the apparatus has problems of high power consumption and risk of electric shock, generating noise and an odor upon electric shock of an insect, and scattering an insect pollutant or a fragment thereof.

In order to solve such problems of the electric insecticidal apparatus, an insect trap using a flypaper-type adhesive sheet has been developed. However, this insect trap has problems in that an insect trapped in the insect trap is seen from the outside, providing an unpleasant feeling to a user, in that a light source mounted on the insect trap has significantly low attraction efficiency, in that the adhesive sheet is likely to adhere to the insect trap upon insertion into the insect trap, or in that the adhesive sheet is easily released after insertion into the insect trap.

Furthermore, there is demand for an insect trap including a cover detachably attached to a main body for repair, replacement and cleaning of components therein. However, a typical insect trap including a detachable cover has a problem in that detachment/attachment of the cover is not easy or the cover is not firmly secured to main body upon recoupling of the cover to the main body.

SUMMARY

Embodiments of the present disclosure provide an adhesive-type insect trap that collects insects by attracting the insects to move towards the insect trap using a light source and has high trapping efficiency while preventing the insects from being directly visibly observed from the outside.

Embodiments of the present disclosure provide an adhesive-type insect trap that prevents an adhesive sheet from being attached to the insect trap upon insertion into the insect trap and that allows the adhesive sheet to be secured to a main body of the insect trap after insertion into the insect trap.

Embodiments of the present disclosure provide an adhesive-type insect trap that includes a photocatalyst generating a deodorization effect.

Embodiments of the present disclosure provide an adhesive-type insect trap that can generate not only light but also a gas such as carbon dioxide, as an element for attraction of insects.

Embodiments of the present disclosure provide an adhesive-type insect trap that is provided with a light source for sterilization capable of sterilizing the interior of the insect trap or killing insects trapped by an adhesive sheet.

Embodiments of the present disclosure provide an adhesive-type insect trap that is provided with a camera capable of observing or photographing insects collected therein.

Embodiments of the present disclosure provide an adhesive-type insect trap that is provided with a sensor for detecting the kind of insect trapped therein, an area of an adhesive sheet trapping insects, brightness of the adhesive sheet, an ambient temperature or illuminance of a light source, the intensity of light emitted from the light source, presence of the adhesive sheet in the insect trap, attachment of a cover to the insect trap, and the like, for adjusting the intensity of light emitted from the light source, or for supplying electric power to the light source depending upon the presence of the adhesive sheet in the insect trap or the attachment of the cover to the insect trap.

Embodiments of the present disclosure provide an adhesive-type insect trap that further includes an insect attractant spray or includes an insect attractant contained in an adhesive sheet to improve insect attraction efficiency.

Embodiments of the present disclosure provide an adhesive-type insect trap that allows easy coupling and separation between a cover and a main body while enabling the cover to be more firmly coupled to the main body.

Embodiments of the present disclosure provide an adhesive-type insect trap that can prevent loss of a cover when the cover is separated from a main body.

Figure 1:
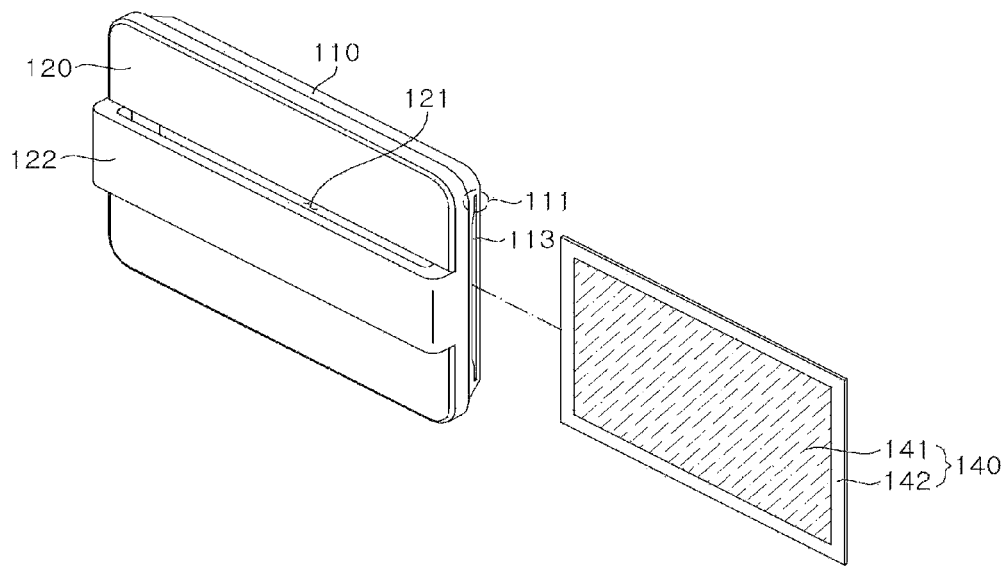
FIG. 1 and FIG. 2 show an embodiment of an adhesive-type insect trap according to the present disclosure.

Detailed Description of Embodiments It should be understood that the present disclosure may be embodied in different ways and is not limited to the following embodiments, which are provided for complete disclosure and thorough understanding of the present disclosure by those skilled in the art.

Herein, when an element such as a layer or a film is referred to as being placed "on" or "under" another element, it can be directly placed "on" or "under" the other element, or intervening element(s) may be present therebetween. Herein, spatially relative terms such as "upper" and "lower" are defined with reference to the accompanying drawings. Thus, it will be understood that the term "upper surface" can be used interchangeably with the term "bottom surface".

Like components will be denoted by like reference numerals throughout the accompanying drawings. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

As used herein, the term "insect" may refer to various kinds of flying insects, particularly flies, without being limited thereto, and a light source may be selected from various kinds of light sources, for example, a UV LED, without being limited thereto.

In addition, as used herein, the term "guide unit" refers to a structure adapted to guide an adhesive sheet from the outside of an insect trap into a main body thereof or to guide the adhesive sheet inside the main body. For example, the guide unit may refer to at least one of a guide groove and a guide rail, in which the guide groove refers to a space through which the adhesive sheet is introduced into the main body, and the guide rail guides the adhesive sheet inside the main body.

One aspect of the present disclosure provides an adhesive-type insect trap including: a main body having an adhesive sheet insertion hole; a light source mount disposed on the main body; and a cover detachably attached to the main body and having a through-hole formed in at least a portion thereof, wherein the adhesive sheet includes a flypaper piece and a sheet, the main body includes a guide unit guiding the adhesive sheet, and the cover includes a light refracting portion formed on an outer surface thereof or an inner surface thereof.

In one embodiment, the light refracting portion may include a light refracting agent and the light refracting agent may include a cured product of at least one of titanium dioxide ($TiO_2$), calcium carbonate ($CaCO_3$) and calcium phosphate ($Ca_3(PO_4)_2$).

In one embodiment, the light refracting portion may include a form in which the light refracting agent is applied to the cover.

In one embodiment, the light refracting portion may include a light refracting agent film in which the light refracting agent is attached to the cover.

In one embodiment, the light refracting portion may include a roughness portion.

In one embodiment, the cover may include the roughness portion formed on the outer surface thereof.

In one embodiment, the cover may include the roughness portion formed on the inner surface thereof.

In one embodiment, the roughness portion may include a base and a protrusion protruding from the base.

In one embodiment, the base may be attached to a surface of the cover.

In one embodiment, the protrusion may be attached to a surface of the cover.

In one embodiment, the roughness portion may include a first protrusion and a second protrusion attached to the first protrusion, and the first protrusion and the second protrusion may have different volumes.

In one embodiment, the light refracting portion may have a haze of 30% or more.

In one embodiment, the light refracting portion may have a difference of less than 40% between total light transmittance (%) and haze (%).

In one embodiment, the adhesive-type insect trap may further include a light source for sterilization.

Another aspect of the present disclosure provides an adhesive-type insect trap including: a main body having an adhesive sheet insertion hole; a light source mount disposed on the main body; and a cover detachably attached to the main body and having a through-hole formed in at least a portion thereof, wherein the adhesive sheet includes a flypaper piece and a sheet, the main body includes a guide unit guiding the adhesive sheet, the cover includes at least one first coupling portion formed on an inner surface thereof, and the main body includes at least one first receiving portion formed on a front surface thereof such that the at least one first coupling portion is coupled to the first receiving portion when the cover is coupled to the main body.

In one embodiment, the first coupling portion may include a first support portion and a first hook portion, the first receiving portion may include a first guide portion and a first catch portion, and the first hook portion may be caught by the first catch portion when the cover is coupled to the main body.

In one embodiment, the first hook portion may be bent towards the inner surface of the cover and may include a distal end having a greater thickness than other portions of the first hook portion.

In one embodiment, the first support portion may include first assistant support portions protruding from the first support portion and adjoining the inner surface of the cover.

In one embodiment, the inner surface of the cover further may include at least one second coupling portion, the front surface of the main body may include at least one second receiving portion, and the at least one second coupling portion may be coupled to the second receiving portion when the cover is coupled to the main body.

In one embodiment, the second coupling portion may include a second support portion and a second hook portion, the second receiving portion may include a second guide portion and a second catch portion, and the second hook portion may be caught by the second catch portion when the cover is coupled to the main body.

In one embodiment, the second hook portion further may include a magnet member, the second receiving portion further may include a magnetic coupling portion, and the magnet member may be coupled to the magnetic coupling portion by magnetic force when the cover is coupled to the main body.

In one embodiment, the adhesive-type insect trap may further include a fastening member connecting the cover to the main body.

In one embodiment, the adhesive-type insect trap may further include a light source for sterilization.

Hereinafter, embodiments of the present disclosure will be described in more detail with reference to the accompanying drawings.

FIG. 1 shows an adhesive-type insect trap according to one embodiment of the present disclosure. Referring to FIG. 1, an adhesive-type insect trap 1000 includes a main body 110 and a cover 120, and may receive an adhesive sheet 140 inserted therein.

The main body 110 may have a shape corresponding to a shape of the adhesive sheet 140 guided into the main body 110 instead of having a particular shape. For example, the main body 110 may include a casing having a hexahedral shape in which an adhesive sheet 140 having a plate shape is guided, and may be formed of a plastic material generally used in the art in order to allow the insect trap to be used indoors or outdoors for a long period of time while preventing excessive increase in manufacturing costs, without being limited thereto.

In addition, the main body 110 includes an adhesive sheet insertion hole 113 formed on a front surface of the main body 110 such that the adhesive sheet 140 can be inserted in an upright posture into the main body 110 in a vertically sliding manner or in a horizontally sliding manner, and a guide groove 111 formed on at least one side of the adhesive sheet insertion hole 113 to guide the adhesive sheet 140. The guide groove 111 may be configured to receive an edge of the adhesive sheet 140 inserted into the main body 110, may have a thickness corresponding to a thickness of the adhesive sheet 140 to allow easy insertion and separation of the adhesive sheet 140 and a depth corresponding to a length preventing a flypaper piece 141 of the adhesive sheet 140 from contacting the main body 110. By way of example, the adhesive sheet insertion hole 113 may have an open shape or a closed shape opened or closed by a door (not shown), which may have any shape and may be configured to block or open at least a portion of the adhesive sheet insertion hole 113.

The cover 120 may have any shape without being limited to a particular shape and may be detachably attached to a front side of the main body 110. The cover 120 may have a through-hole 121 formed in at least a portion thereof to allow insects to pass therethrough, may be formed of a material allowing light emitted from a light source 170 mounted on a light source mount 130 to pass therethrough, and may have a roughened surface or may include a separate cover sheet attached to or spaced apart from a front side or a rear side of the cover 120 to allow refraction or diffusion of the light. The cover 120 may be rotatably disposed on the main body 110 such that a user can change the location of the cover 120 depending upon user environment. Further, the cover 120 may be detachably attached to the main body 110 through sliding movement or by a magnet in order to prevent damage to components of the adhesive-type insect trap 1000 such as the adhesive sheet 140 and the like due to application of excessive force to the cover 120 to separate the cover 120 from the main body 110 by a user. Further, the cover 120 may be connected to the main body 110 through a ring, a chain or a string formed of a stretchable material. Alternatively, the cover 120 may be secured at one side thereof to the main body 110 and detachably coupled at the other side thereof to the main body 110 to prevent the cover 120 from being completely separated from the main body 110.

By way of example, at least a portion or the entirety of the cover 120 may be formed of a light transmissive material. For example, a portion of the cover 120 through which light emitted from the light source 170 passes may comprise polycarbonate (PC), polyethylene terephthalate (PET), methacrylate-styrene (MS), poly(methyl methacrylate) (PMMA), or the like, and may have at least one of transparent, translucent and opaque colors.

The cover 120 may have a through-hole blocking structure 122 adapted to block at least a portion of the through-hole 121. The through-hole blocking structure 122 may have any shape capable of blocking at least a portion of the through-hole 121 and may be integrally formed with the cover 120 or may be detachable from the cover 120. In addition, the through-hole blocking structure 122 may extend from the cover 120 to protrude outward from the cover 120 or may be formed by a convex or concave portion of the cover 120. By way of example, referring to FIG. 1, the through-hole blocking structure 122 may be realized by a protruded portion relative to the cover 120.

That is, the adhesive-type insect trap 1000 has the through-hole blocking structure 122 adapted to block the adhesive sheet 140 from being visible from the outside, thereby preventing insects attached to the adhesive sheet 140 from being observed from the outside.

The adhesive sheet 140 may include a flypaper piece 141 applied to or coated onto a sheet 142. For example, the flypaper piece 141, which is a pressure sensitive adhesive material, is applied to or coated on one surface of a paper sheet to trap insects attached to the adhesive material. Here, instead of being applied to or coated onto the entire surface of the sheet 142, the flypaper piece 141 may be partially applied to or coated onto the sheet 142 to expose at least a portion of the sheet 142 such that a user can easily replace the adhesive sheet without a separate gripper formed on the sheet 142 while preventing the flypaper piece 141 from being adhered to the adhesive sheet insertion hole 113 or the guide groove 111.

Figure 2:
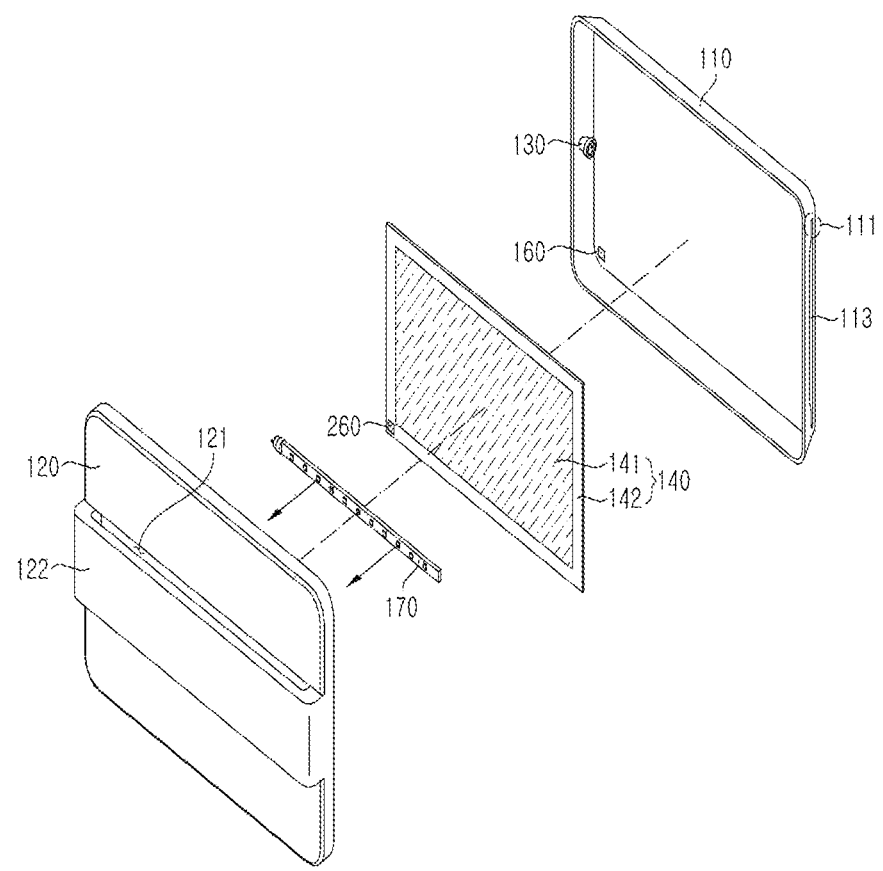

Referring to FIG. 2, the main body 110 and the adhesive sheet 140 may include magnet members 160, 260 disposed to face each other and having opposite polarities, respectively. That is, the adhesive sheet 140 may be prevented from being separated from the main body even upon rotation of an adhesive-type insect trap 2000 after installation of the adhesive sheet 140 to the main body 110 by a user.

Referring again to FIG. 2, the adhesive-type insect trap 2000 may further include the light source mount 130 received in the main body 110. The light source mount 130 is provided with the light source 170, which not only acts as a lighting fixture but also emits light for attraction of insects or UVC for sterilization of insects or bacteria in the insects collected in the insect trap. The light source mount 130 may include a socket and may be disposed in any direction including a longitudinal direction and a transverse direction.

The light source 170 emits light having a wavelength capable of attracting insects and the main body 110 may include at least one light source therein. For example, the light source 170 may emit UV light having a wavelength of 350 nm to 400 nm, at which the light source 170 can efficiently attract insects exhibiting positive phototaxis to move from the periphery to bright light, thereby improving insect attraction efficiency without providing harmful influence to a user body.

The adhesive sheet 140 may be provided to at least one of a front side, a rear side and lateral sides of the light source mount 130 and may be formed of a transparent material or an opaque material depending upon installation locations of the adhesive sheet 140 and the light source mount 130. For example, when light emitted from the light source 170 is emitted outside the cover 120 after passing through the adhesive sheet 140, both the flypaper piece 141 and the sheet 142 of the adhesive sheet 140 may be formed of a light transmissive material or at least one of the flypaper piece 141 and the sheet 142 may be formed of a light transmissive material, for example, a material having high UV light transmittance, to allow light emitted from the light source 170 to pass therethrough.

Figure 3:
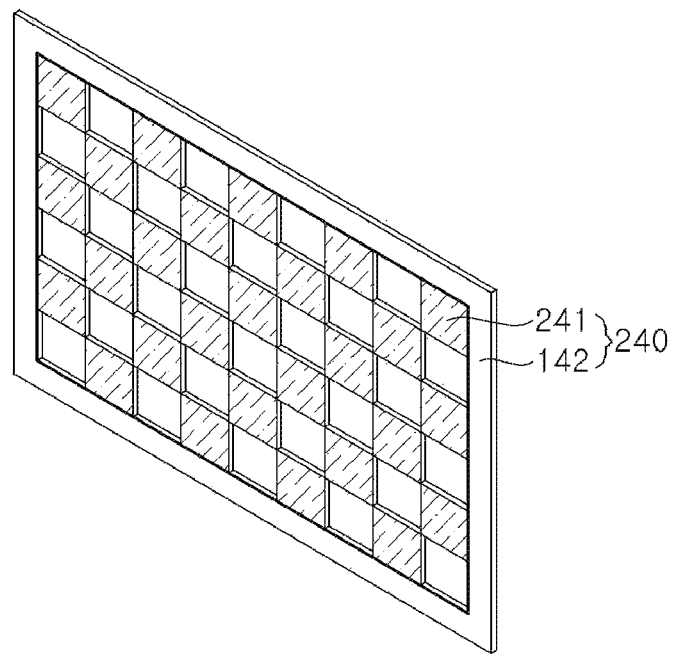
FIG. 3 and FIG. 4 show embodiments of the adhesive-type insect trap according to the present disclosure, respectively.
Figure 4:
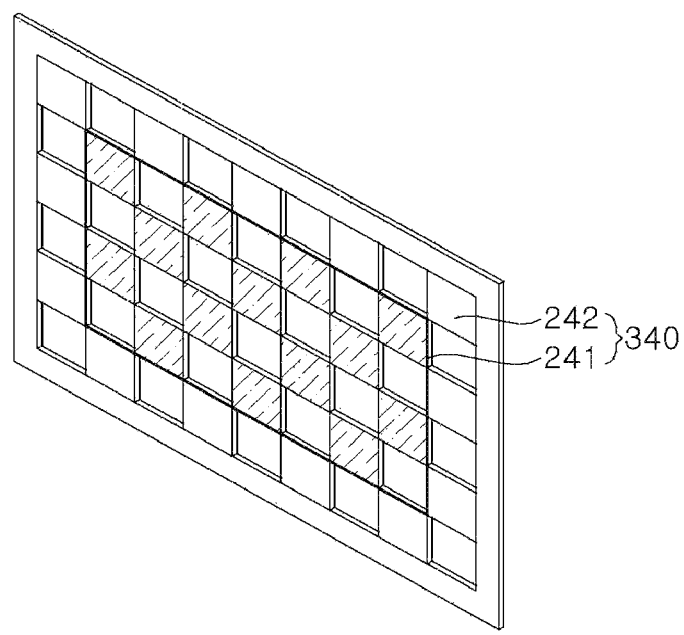

For example, referring to FIG. 3, an adhesive sheet 240 includes a sheet 142 formed of a transparent material and a flypaper piece 241 formed of an opaque material. In this example, the flypaper piece 241 may be disposed in a lattice shape or may be disposed to form punching holes. Alternatively, referring to FIG. 4, in an adhesive sheet 340, both a sheet 242 and the flypaper piece 241 may be disposed in a lattice shape or may be disposed to form punching holes, and the punching holes formed through the sheet 242 and the flypaper piece 241 at least partially overlap each other to allow light emitted from the light source 170 to pass therethrough. Here, each frame of the lattice shape may have a smaller size than insects, for example, flies, and may have a length of 2 mm to 8 mm.

FIG. 5 to FIG. 10 show various embodiments of the light source 170 and the adhesive sheet 140 disposed on an adhesive-type insect trap 3000, 4000, 5000, 6000, 7000 or

8000. In this drawings, the light source 170 is shown instead of the light source mount 130, in order to allow a person having ordinary knowledge in the art to clearly understand arrangement of the light source 170 and the adhesive sheet 140 on each insect trap. The light source 170 may be a sheet light source or a spot light. In FIG. 5 through FIG. 10, a spot light source is shown by way of example.

Figure 5:
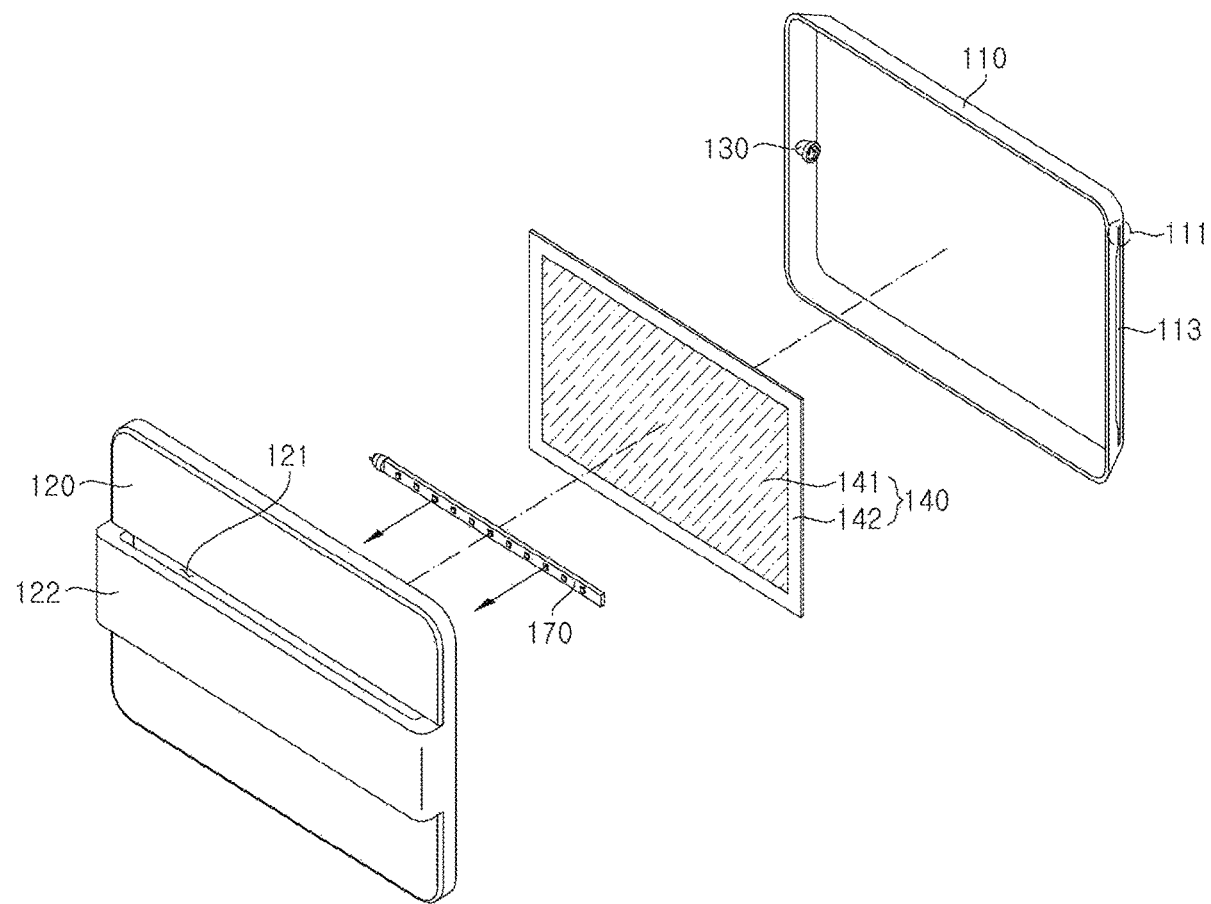
FIG. 5 shows an adhesive-type insect trap having a light source disposed in a space between an adhesive sheet and a cover according to an embodiment of the present disclosure.

Referring to FIG. 5, in the adhesive-type insect trap 3000, the light source 170 may be disposed in a space between the adhesive sheet 140 and the cover 120 such that light emitted from the light source 170 is directed towards the cover 120, and the adhesive sheet 140 may be formed to allow or prevent light transmission therethrough. The adhesive-type insect trap 3000 does not require additional reflectors 150, 250, a reflective sheet 143, or the flypaper pieces 141, 241, thereby enabling reduction in manufacturing costs.

Figure 6:
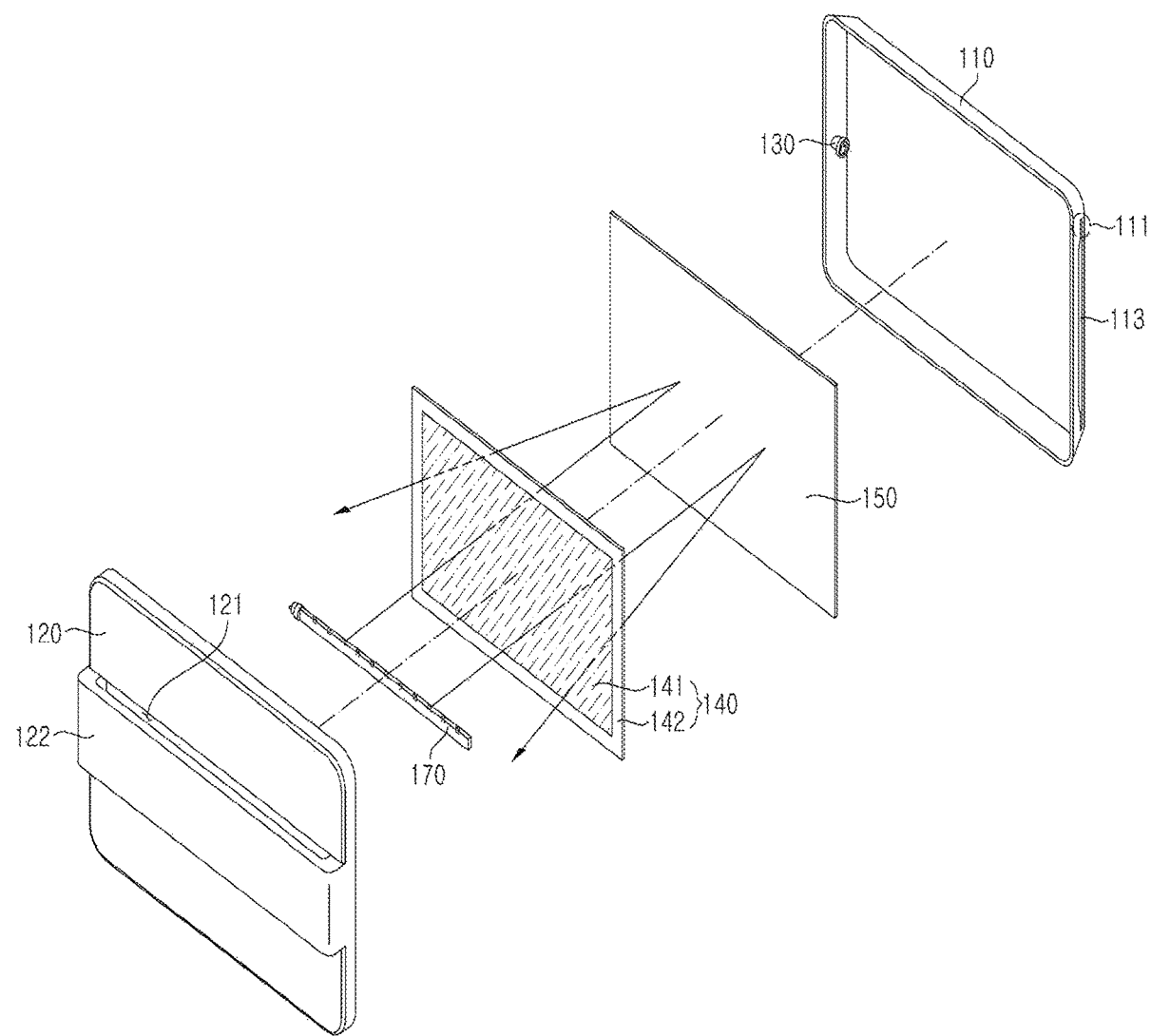
FIG. 6 shows an adhesive-type insect trap having a light source disposed in a space between an adhesive sheet and a cover and having a reflector between the adhesive sheet and a main body according to an embodiment of the present disclosure.

Referring to FIG. 6, the adhesive-type insect trap 4000 may further include a reflector 150 disposed between the adhesive sheet 140 and the main body 110, in which the light source 170 may be disposed in a space between the adhesive sheet 140 and the cover 120 such that light emitted from the light source 170 is directed towards the main body 110. As described above, the adhesive sheet 140 may be formed of a light transmissive material or may partially have a lattice shape to allow light emitted from the light source 170 to pass therethrough. Insects, particularly flies, tend to be more strongly attracted to refracted or diffused light than to direct light. Thus, the adhesive-type insect trap 4000 is configured to allow light emitted from the light source 170 to pass through the adhesive sheet 140 at least once, instead of directly passing through the cover, thereby improving insect attraction efficiency with decoy light.

Figure 7:
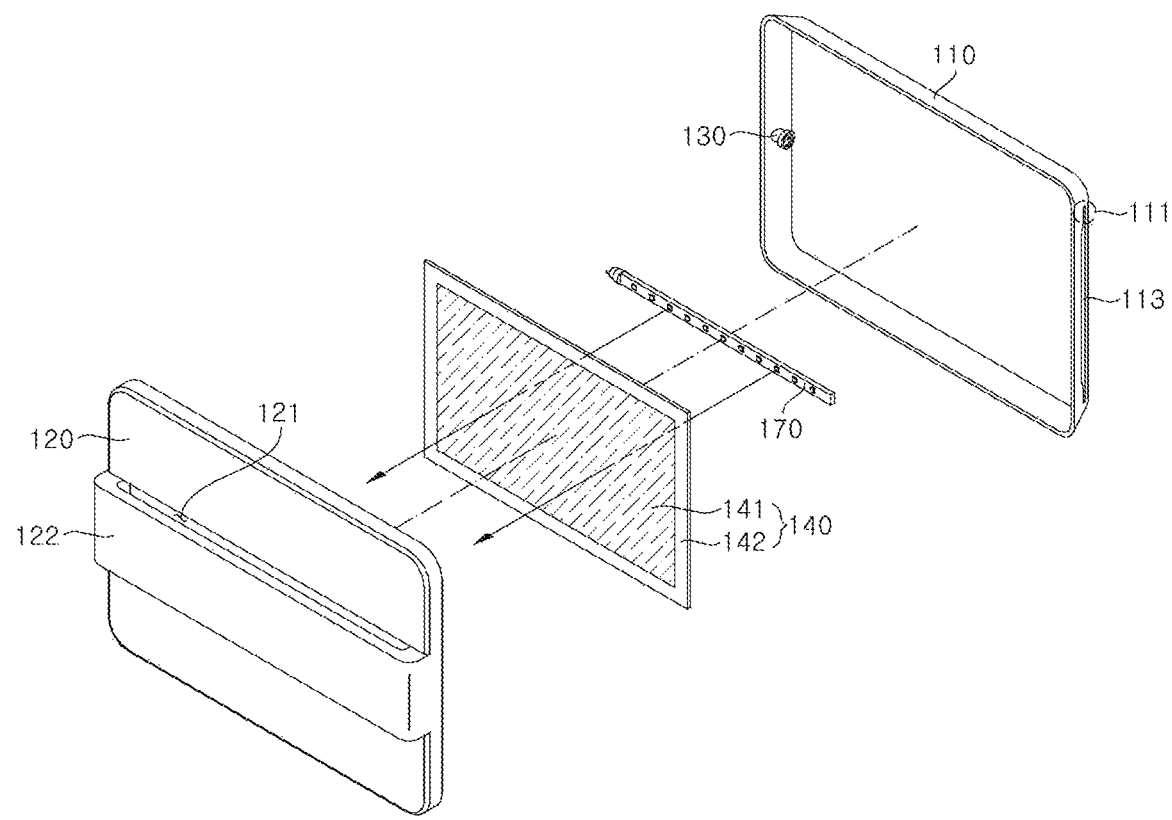
FIG. 7 shows an adhesive-type insect trap having a light source disposed in a space between an adhesive sheet and a main body according to an embodiment of the present disclosure.

Referring to FIG. 7, the adhesive-type insect trap 5000 includes the light source 170 disposed in a space between the adhesive sheet 140 and the main body 110 such that light emitted from the light source 170 is directed towards the adhesive sheet 140 and the cover 120 to be refracted or spread instead of directly irradiating insects, thereby improving insect attraction efficiency with decoy light.

Figure 8:
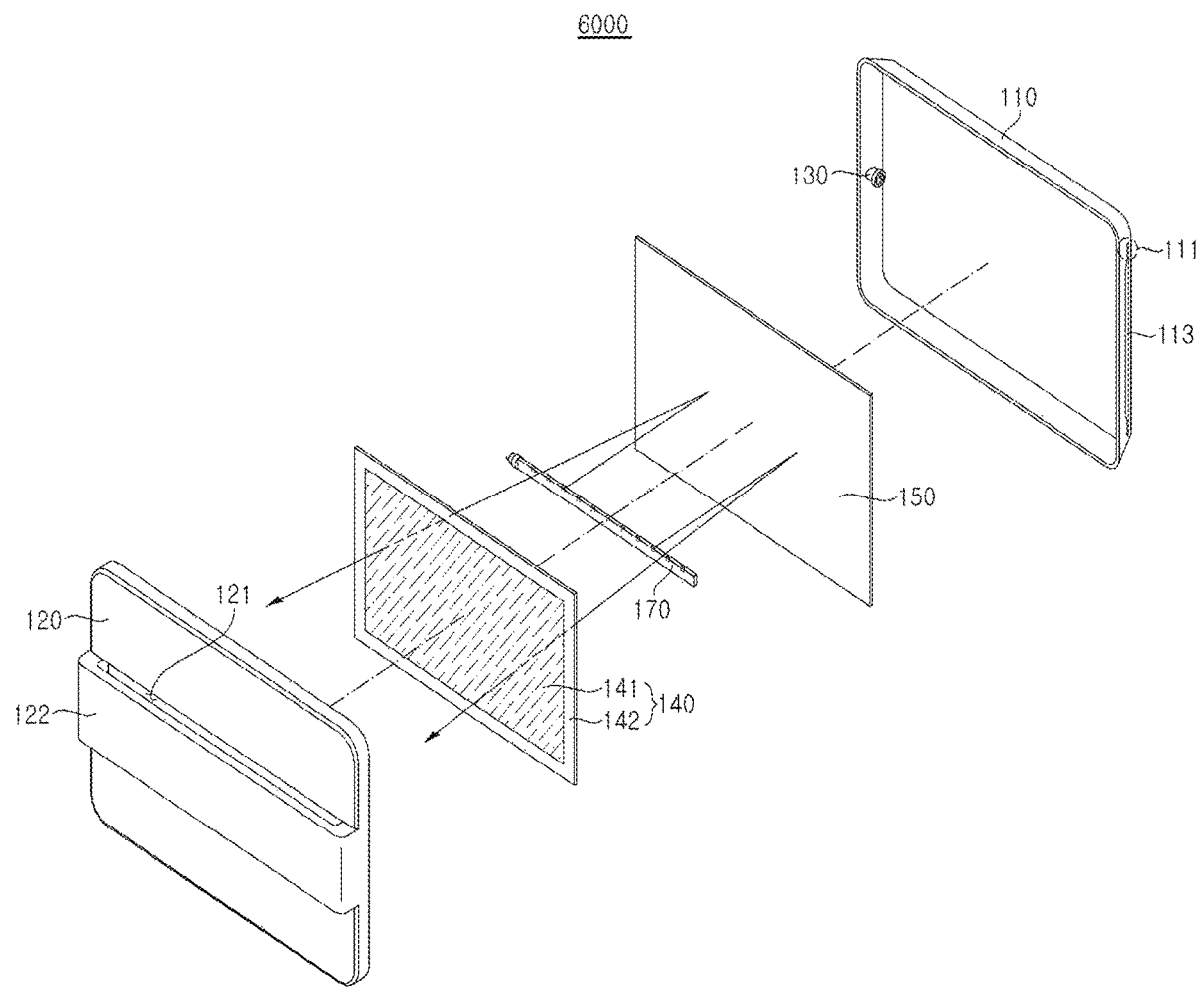
FIG. 8 shows an adhesive-type insect trap having a light source and a reflector between an adhesive sheet and a main body according to an embodiment of the present disclosure.

Referring to FIG. 8, the adhesive-type insect trap 6000 may further include the reflector 150 between the light source 170 and the main body 110, in which the light source 170 may be disposed in a space between the adhesive sheet 140 and the reflector 150 such that light emitted from the light source 170 is directed towards the reflector 150. With the structure that prevents light from directly reaching the adhesive sheet 140 and insects while allowing the light to be refracted or spread, the flypaper piece applied to the adhesive sheet 140 can be prevented from being deformed by light or heat while improving insect attraction efficiency with decoy light.

The adhesive-type insect trap 7000 or 8000 may include a plurality of light sources 170, which may be disposed in a direction in which the flypaper piece 141 of the adhesive sheet 140 is disposed, in an opposite direction thereto, or on a side surface. By way of example, referring to FIG. 9, in the adhesive-type insect trap 7000, the plural light sources 170 are disposed to face each other in opposite directions such that light emitted from one light source 170 is directed to another light source 170 disposed in an opposite direction to the one light source 170, and each reflector 250 may be disposed in an opposite direction to a direction in which each light source 170 emits light. By way of example, the reflector 250 includes a flat reflective surface and a bent portion formed at each side of the reflective surface except for sides of the reflective surface adjacent to the cover to allow light to be directed towards the cover. By way of example, the adhesive-type insect trap 7000 includes the plurality of light sources 170 disposed in a space between the adhesive sheet 140 and the main body 110, and allows light emitted from each of the light sources 170 to sequentially pass through the adhesive sheet 140 and the cover 120 after being reflected by the reflector 250 disposed at a rear side of the light source 170 disposed in an opposite direction thereto, thereby improving insect attraction efficiency through refraction and diffusion of light.

Figure 9:
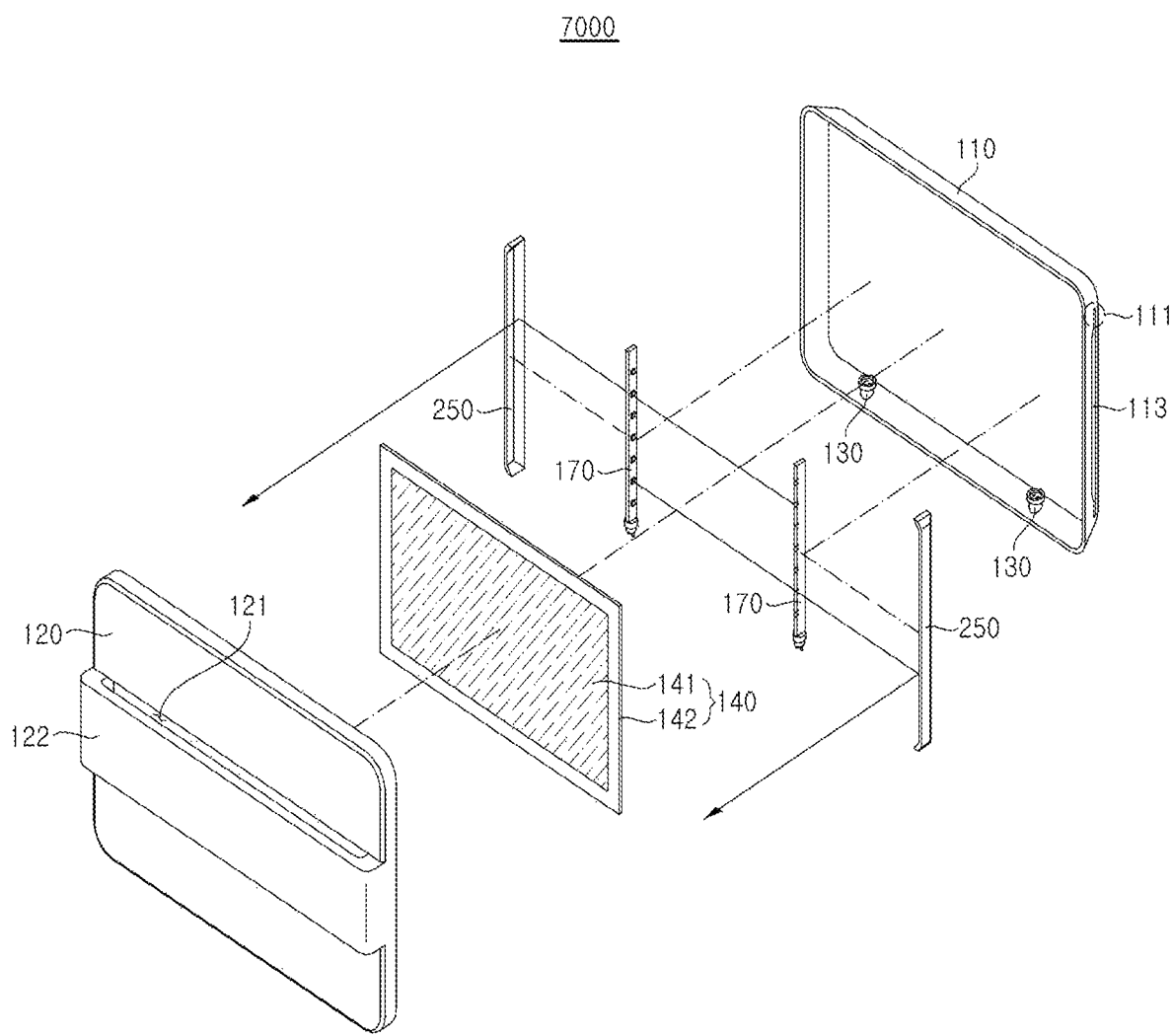
FIG. 9 shows an adhesive-type insect trap having plural light sources according to an embodiment of the present disclosure.
Figure 10:
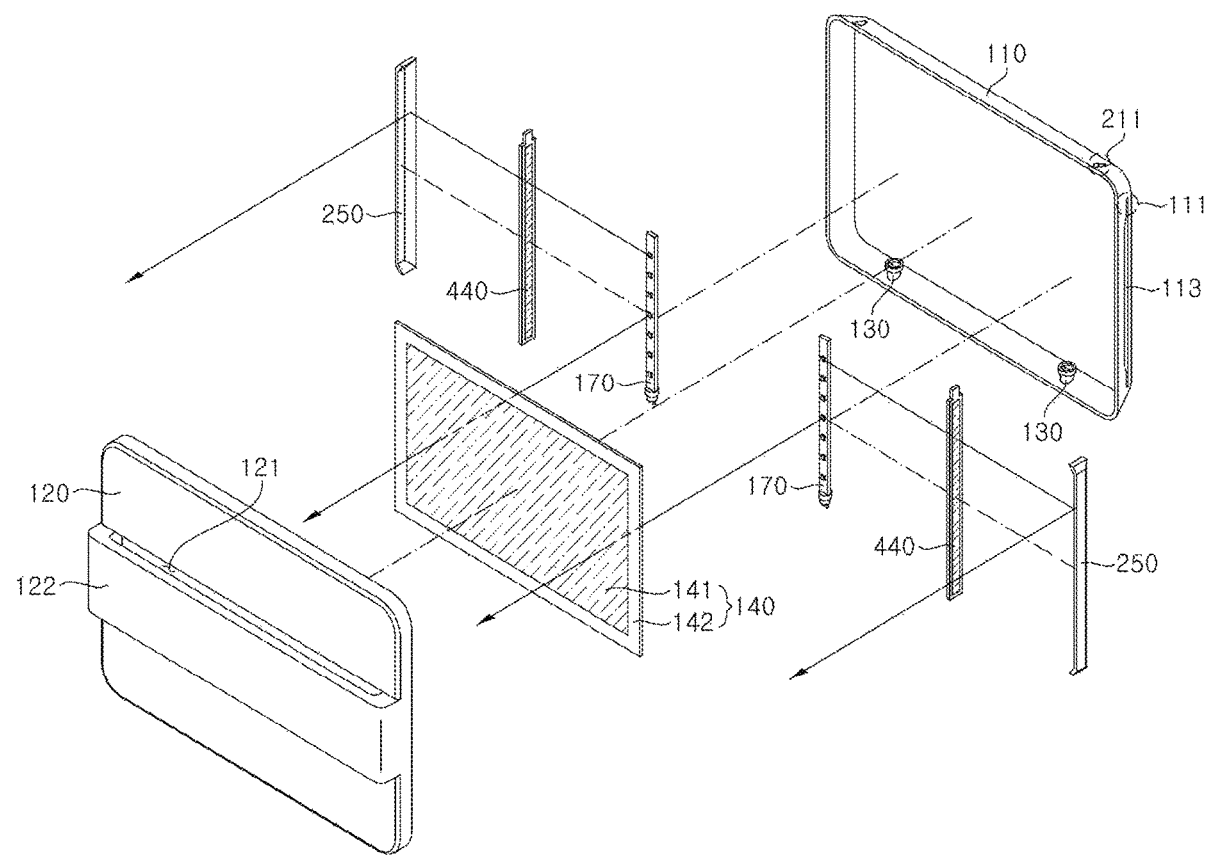
FIG. 10 shows an adhesive-type insect trap having a different light emission direction than the adhesive-type insect trap of FIG. 9 and having additional adhesive sheets according to an embodiment of the present disclosure.

Referring to FIG. 10, the adhesive-type insect trap 8000 has a different light emission direction than the adhesive-type insect trap 7000 shown in FIG. 9 and may further include additional adhesive sheets 440. For example, the adhesive-type insect trap 8000 may further include the adhesive sheets 440, each of which is disposed between the light source 170 and the reflector 250 along a guide groove 211 formed on the main body 110, such that each of the light sources 170 emits light towards the reflector 250 adjacent thereto and the adhesive sheet 140 disposed corresponding to the front side of the main body 110. That is, the adhesive-type insect trap 8000 allows light emitted from the light sources 170 to be refracted and spread, thereby improving insect attraction efficiency with decoy light, and is provided with the adhesive sheets 440 not only at the front side of the main body 110 but also at lateral sides thereof, thereby improving insect trapping efficiency and capacity.

On the other hand, the adhesive-type insect trap 3000, 4000, 5000, 6000, 7000 or 8000 shown in FIG. 5 through FIG. 10 may include the plurality of light sources 170, at least one of which may emit UVC light. Accordingly, the adhesive-type insect trap 3000, 4000, 5000, 6000, 7000 or 8000 according to the embodiments of the disclosure includes a UVC light source disposed to emit UVC light towards the adhesive sheet 140, 240, 340 or 440 and the interior of the adhesive-type insect trap 3000, 4000, 5000, 6000, 7000 or 8000, thereby rapidly killing insects and sterilizing or neutralizing bacteria contained in the insects or generated within the adhesive-type insect trap 3000, 4000, 5000, 6000, 7000 or 8000. In FIG. 5 through FIG. 10, the plurality of light sources 170 is described for convenience of explanation, but different light sources may be used based on different arrangements of a reflector, an adhesive sheet, or other parts of the adhesive-type insect traps.

Figure 11:
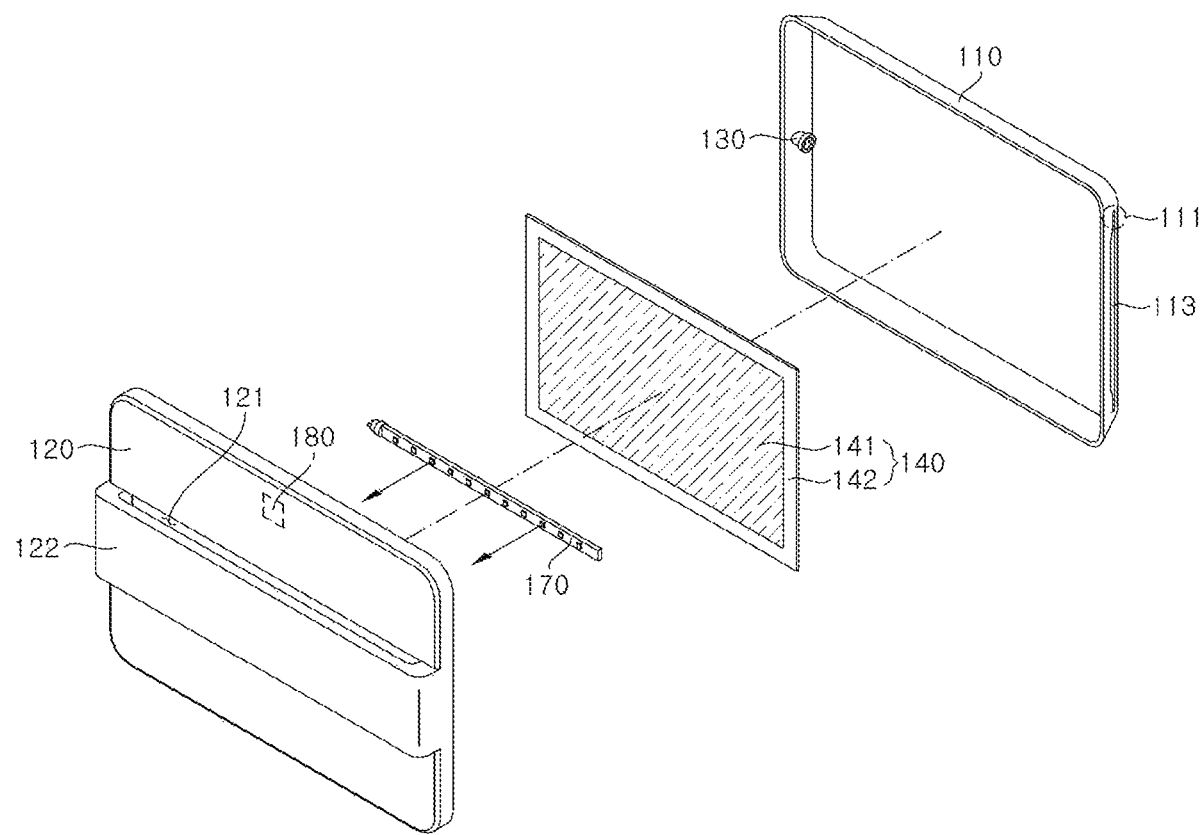
FIG. 11 shows an embodiment of the adhesive-type insect trap having a sensor according to an embodiment of the present disclosure.
Figure 12:
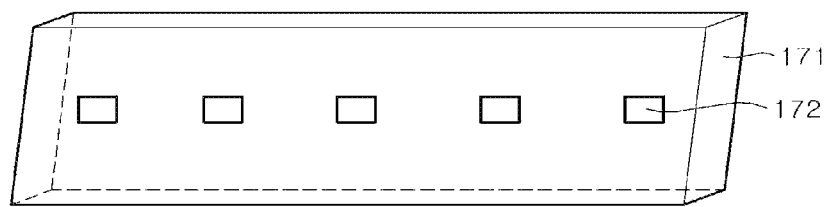
FIG. 12 shows a light source having a single support member according to an embodiment of the present disclosure.
Figure 13:
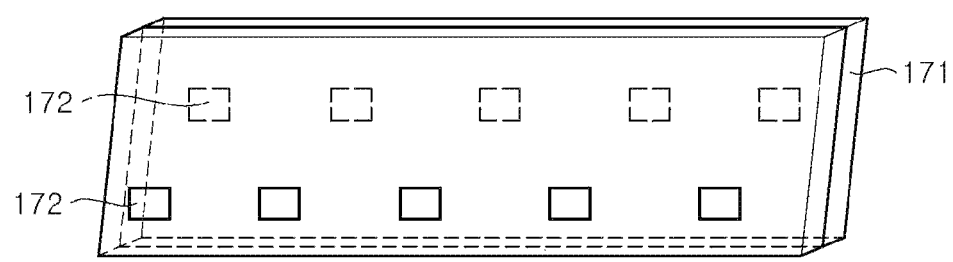
FIG. 13 shows a light source having a stack of support members according to an embodiment of the present disclosure.
Figure 14:
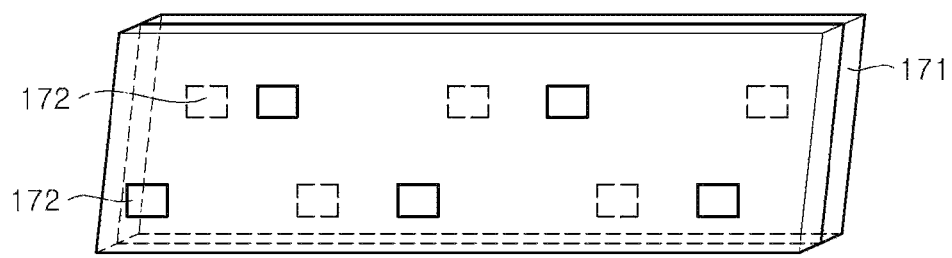
FIG. 14 shows a light source having a different arrangement of light emitting diodes from FIG. 13 according to an embodiment of the present disclosure.

Referring to FIG. 11, an adhesive-type insect trap 9000 may further include a sensor 180. The sensor 180 may detect at least one of the kind of insect trapped on the adhesive sheet 140, an area of the adhesive sheet 140 trapping insects, brightness of the adhesive sheet 140, an ambient temperature of the light source 170, intensity of light emitted from the light source 170, illuminance of ambient light around the insect trap 9000, insertion of the adhesive sheet 140 into the insect trap, and attachment of the cover 120 to the insect trap 9000.

In one embodiment, the sensor 180 may include a UV sensor capable of detecting the intensity of light emitted from the light source 170 to display an alarm message to a user before lifespan of the light source 170 is finished. The alarm message may be displayed through a separate lamp (not shown) or a separate sound generator (not shown) mounted on the adhesive-type insect trap 9000.

In another embodiment, the sensor 180 may include an illuminance sensor capable of detecting illuminance of surrounding light around the adhesive-type insect trap 9000. For example, the illuminance sensor may be set to have at least one preset illuminance range of the surrounding light and the intensity of light emitted from the light source 170 may be automatically controlled depending upon the illuminance range of the surrounding light. In addition, the adhesive-type insect trap 9000 may further include a luminous intensity regulator (not shown) for regulation of the luminous intensity of the light source 170 to display a desirable luminous intensity of the light source 170 depending upon the illuminance range such that a user can manually regulate the luminous intensity. That is, the adhesive-type insect trap 9000 controls the light source 170 to emit light having suitable intensity for insect attraction, thereby enabling efficient power consumption.

In a further embodiment, the adhesive-type insect trap 9000 may further include a temperature sensor (not shown). The temperature sensor may detect heat generated from the light source 170 mounted on the adhesive-type insect trap 9000 to stop power supply to the light source 170 when the temperature increases above a preset temperature.

In yet another embodiment, the adhesive-type insect trap 9000 may include a magnetic sensor for detecting whether the adhesive sheet 140 is inserted into the main body and whether the cover 120 is attached thereto to display an alarm message to a user when the adhesive sheet 140 is incompletely inserted or the cover 120 is incompletely attached to the main body 110.

In yet another embodiment, the adhesive-type insect trap 9000 may include a limit sensor. The limit sensor may permit power supply to the light source 170 when the adhesive sheet 140 is inserted into the main body 110 or the cover 120 is attached to the main body 110, and may stop power supply to the light source or display an alarm message to a user, as described above, when the adhesive sheet 140 is incompletely inserted or the cover 120 is incompletely attached to the main body 110.

In yet another embodiment, the adhesive-type insect trap 9000 may include a photosensor for detecting inflow of insects into the main body. When the insects enter the adhesive-type insect trap 9000, the photosensor may display an alarm message to a user, as described above, or supply power to a camera configured to observe insects trapped therein, described below.

FIG. 12 through FIG. 17 show various embodiments of light sources 170, 270, 370, 470, 570, 670, 770 mounted on the light source mount 130 of the adhesive-type insect trap 2000, 3000, 4000, 5000, 6000, 7000, 8000 or 9000.

The light source 170, 270, 370, 470, 570, 670 or 770 may include light emitting diodes 172 attached to a support member 171, 271, 371 or 471. As shown in FIG. 12 to FIG. 16, the light source 170, 270, 370, 470, 570, 670 or 770 may include a single support member 171 or a stack of support members 171. On the stack of support members 171, the light emitting diodes 172 are disposed in a zigzag arrangement to suppress damage to the support members by heat therefrom.

Figure 15:
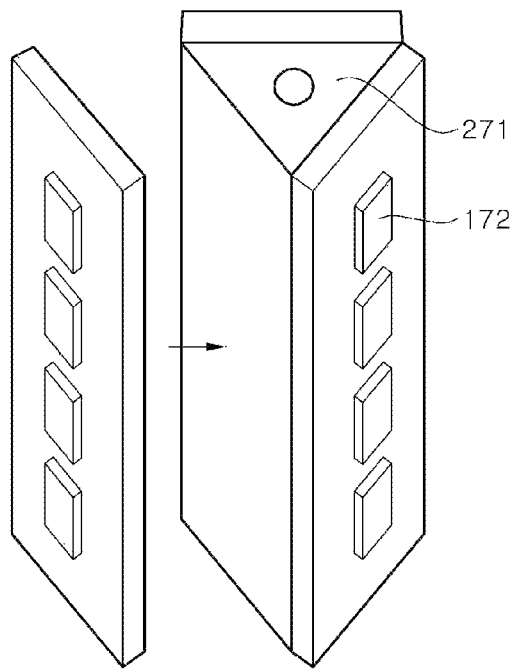
FIG. 15 shows a light source mounted on a polygonal column-shaped support member according to an embodiment of the present disclosure.
Figure 16:
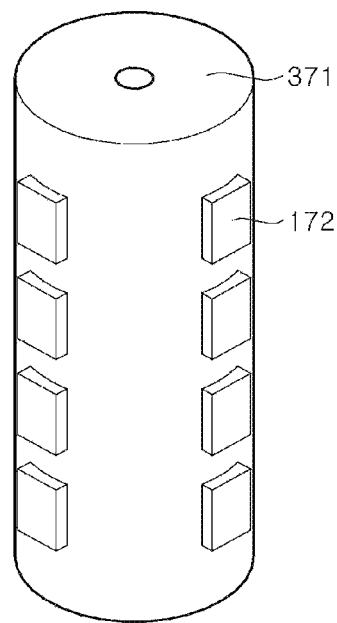
FIG. 16 shows a light source mounted on a cylindrical support member according to an embodiment of the present disclosure.

Referring to FIG. 15 and FIG. 16, the light source 570 or 670 includes the light emitting diodes 172 mounted on a polygonal column-shaped support member 570 or a cylindrical support member 670 to reduce the volume of the adhesive-type insect trap 2000, 3000, 4000, 5000, 6000, 7000, 8000 or 9000 while allowing emission of light in a broad range, thereby improving light irradiation efficiency. By way of example, a triangular support member 570 may be formed by coupling three PCBs in a triangular shape.

In another embodiment, the support member may include a flexible support member. The flexible support member may be entirely or partially bendable. That is, in order to reduce the size of the adhesive-type insect trap 2000, 3000, 4000, 5000, 6000, 7000, 8000 or 9000 according to the embodiments of the disclosure while improving insect attraction efficiency, the light source mount may have a bent shape or may be bendable and the flexible support member may be mounted on a light source mount (not shown) having a bent shape or on a light source mount (not shown) deformed in a bent shape.

Figure 17:
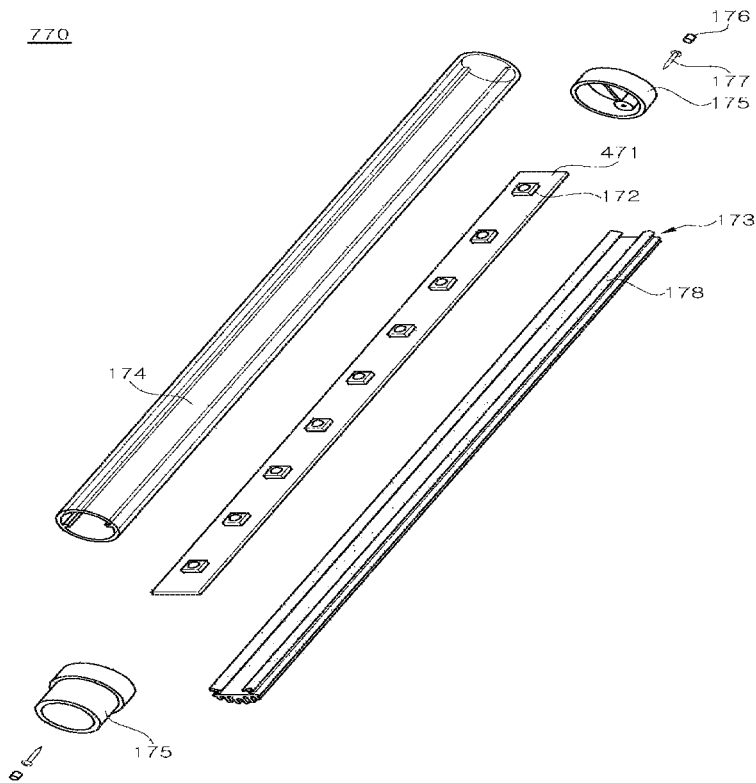
FIG. 17 shows an embodiment of a light source according to the present disclosure.

Referring to FIG. 17, the light source 770 may be a tube type LED. The tube type LED 770 may be electrically connected to an external power supply via wire bonding or without wire bonding. By way of example, the tube type LED 770 has a structure in which light emitting diodes 172 are attached to a support member 471 mounted on one surface of a heat sink 173, and includes a case 174 receiving the support member 471 and the heat sink 173 therein and bases 175 coupled to opposite sides of the case 174. By way of example, the heat sink 173 may further include a support member holder 178 surrounding both sides of the support member 471. At least one surface of the support member holder 178 has a gradually increasing height from an inner side thereof, on which the support member 471 is seated, towards an outer periphery thereof. By way of example, the aforementioned support member 171, 271 or 371 may be mounted on the tube type LED 770. By way of example, the tube type LED 770 may include light emitting diodes 172 attached to both sides of the support member 171 or 471, in which light emitting diodes for insect attraction are attached to one side of the support member and UVC light emitting diodes for sterilization and killing of insects are attached to the other side thereof. For example, the light source 770 may include two tube type LEDs each including 10 light emitting didoes 172. The light source 770 may have a wavelength of 320 nm to 390 nm and a light output of 3,500 mW to 4,500 mW to provide insect attraction efficiency with decoy light.

Figure 18:
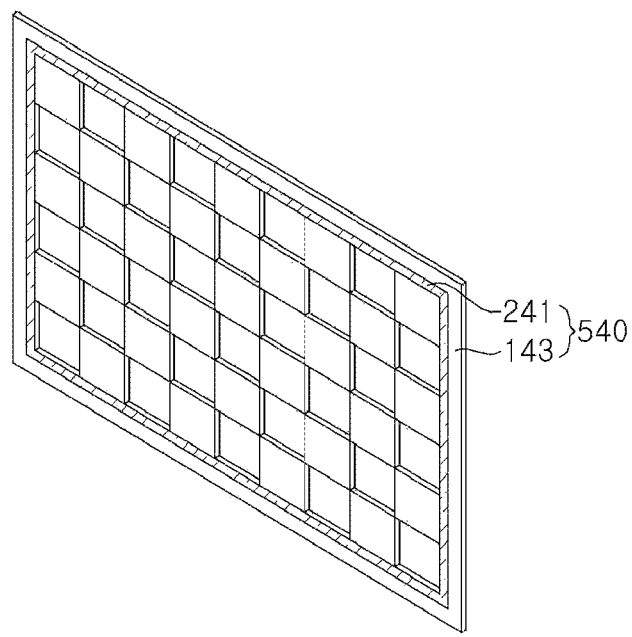
FIG. 18 shows embodiments of an adhesive sheet including a flypaper piece and a reflective sheet according to the present disclosure.

Referring to FIG. 18, in the adhesive-type insect trap 1000, 2000, 3000, 4000, 5000, 6000, 7000, 8000 or 9000, an adhesive sheet 540 includes flypaper pieces 141, 241 and a reflective sheet 143. The reflective sheet 143 may refer to a member on which the flypaper piece 141, 241 are deposited or coated. Here, the flypaper piece 141 may be formed of a light transmissive material to allow light emitted from the light source to pass therethrough and the flypaper piece 241 may include an opaque material. In this case, the flypaper piece 241 may be disposed in a lattice shape on the reflective sheet 143 such that light emitted from the light source 170 is reflected by the reflective sheet 143 to attract insects. That is, the adhesive-type insect trap 1000, 2000, 3000, 4000, 5000, 6000, 7000, 8000 or 9000 may allow light emitted from the light source 170, 270, 370, 470, 570, 670 or 770 to be reflected by the reflective sheet 143 such that the cover 120 can be irradiated in a large area with the light when the light passes through the cover 120, and may guide insects collected in the adhesive-type insect trap 1000, 2000, 3000, 4000, 5000, 6000, 7000, 8000 or 9000 by the reflected light to remain inside the main body 110, thereby improving insect trapping efficiency. Insects, particularly flies, tend to be more strongly attracted to refracted or diffused light than to direct light. Thus, the adhesive-type insect trap 1000, 2000, 3000, 4000, 5000, 6000, 7000, 8000 or 9000 allow light emitted from the light source 170 to be reflected at least once by the reflective sheet 143 instead of directly passing through the cover, thereby improving insect attraction efficiency with decoy light.

Figure 19:
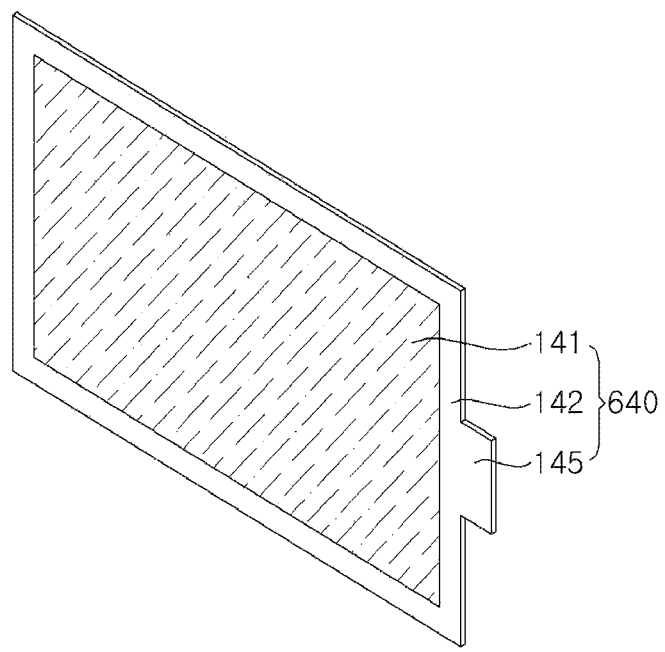
FIG. 19 shows an adhesive sheet including a gripper according to embodiments of the present disclosure.

Referring to FIG. 19, an adhesive sheet 640 includes a gripper 145, which extends a predetermined length therefrom to allow a user to easily grip the gripper 145 upon insertion or separation of the adhesive sheet 640 into or from the adhesive-type insect trap 1000, 2000, 3000, 4000, 5000, 6000, 7000, 8000 or 9000 in a vertical direction or in a horizontal direction. Accordingly, the adhesive sheet 640 may be provided to the adhesive-type insect trap by inserting the adhesive sheet 140 into a space between the main body 110 and the guide groove 111 in a downward direction or in a leftward direction using the gripper 145, and may be replaced by separating the adhesive sheet 640 therefrom in an upward direction or in a rightward direction using the gripper 145.

Referring to FIG. 20 to FIG. 23, adhesive-type insect traps 1100, 1200 may adopt the structure of the adhesive-type insect trap 1000, 2000, 3000, 4000, 5000, 6000, 7000, 8000 or 9000, and the following description will focus on various embodiments of covers 220, 320.

Figure 20:
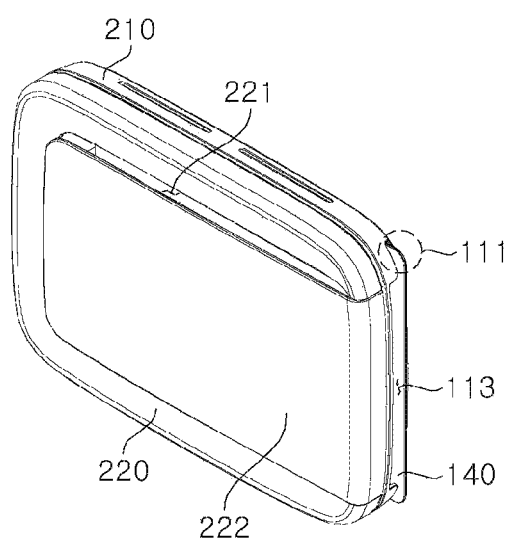
FIG. 20 shows an adhesive-type insect trap having a cover with a through-hole blocking structure according to an embodiment of the present disclosure.
Figure 21:
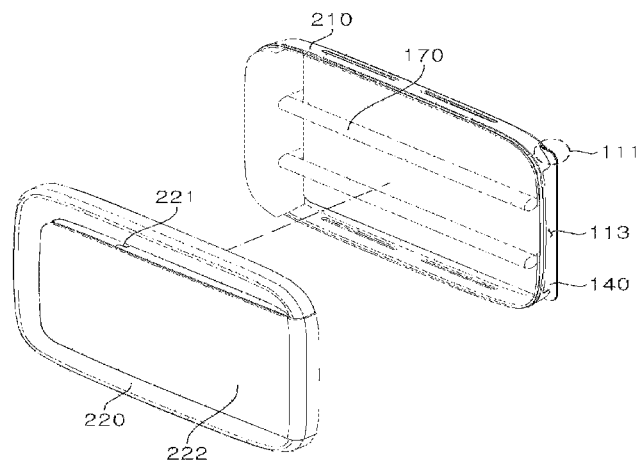
FIG. 21 shows a dissembled state of the adhesive-type insect trap of FIG. 21 according to an embodiment of the present disclosure.

Referring to FIG. 20 and FIG. 21, in the adhesive-type insect trap 1100, the cover 220 may include a through-hole blocking structure 222 adapted to block at least a portion of a through-hole 221, which may be depressed into the cover 220. For example, the through-hole blocking structure 222 may extend from an edge of the cover 220 in a horizontal direction of the cover 220. That is, the adhesive-type insect trap 1100 is configured to maximize the area of the through-hole 221 to improve insect trapping efficiency and to prevent the through-hole blocking structure 222 from protruding from the cover 220 so as to reduce the volume thereof, thereby enabling miniaturization thereof.

Figure 22:
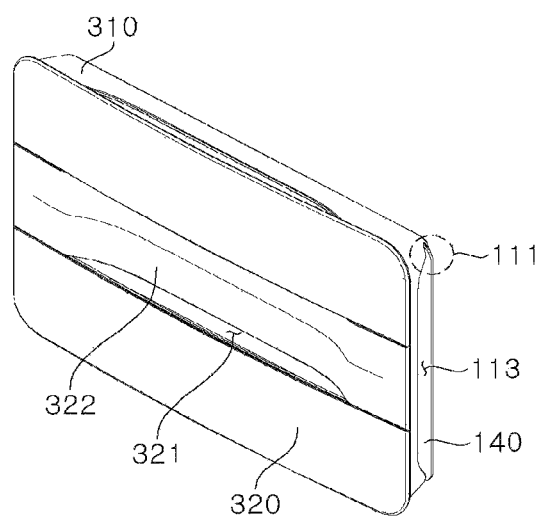
FIG. 22 shows an adhesive-type insect trap showing a cover having a concavely depressed through-hole according to an embodiment of the present disclosure.
Figure 23:
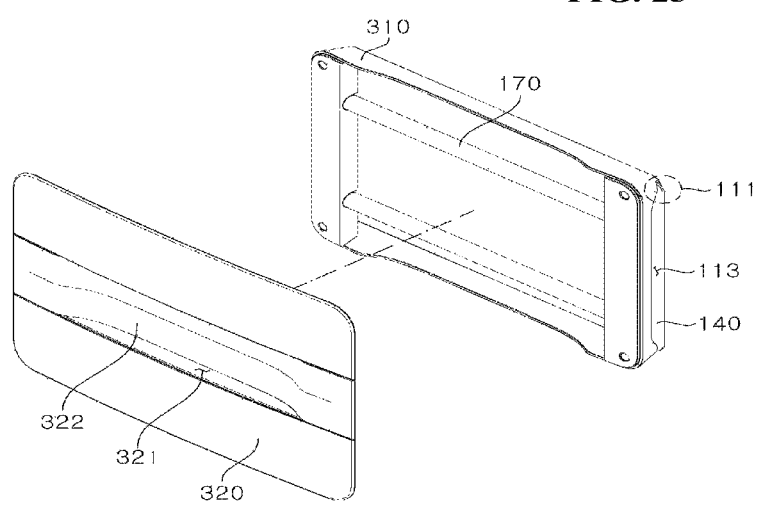
FIG. 23 shows a dissembled state of the adhesive-type insect trap of FIG. 22 according to an embodiment of the present disclosure.

Referring to FIG. 22 and FIG. 23, in the adhesive-type insect trap 1200, the cover 320 may include a through-hole blocking structure 322 adapted to block at least a portion of a through-hole 321, which is concavely depressed into the cover 320. For example, the through-hole blocking structure 322 may be integrally formed with the cover 320 and the through-hole 321 may include a step of the cover 320 formed by the concave shape of the through-hole blocking structure 322. That is, in the adhesive-type insect trap 1200, the through-hole blocking structure 322 prevents the adhesive sheet 140 from being viewed through the through-hole 321 from the outside so as to prevent insects attached to the adhesive sheet 140, 240, 340, 440, 540 or 640 from being observed from the outside and does not protrude outwards from the cover 320, thereby enabling miniaturization of the adhesive-type insect trap 1200.

Figure 24:
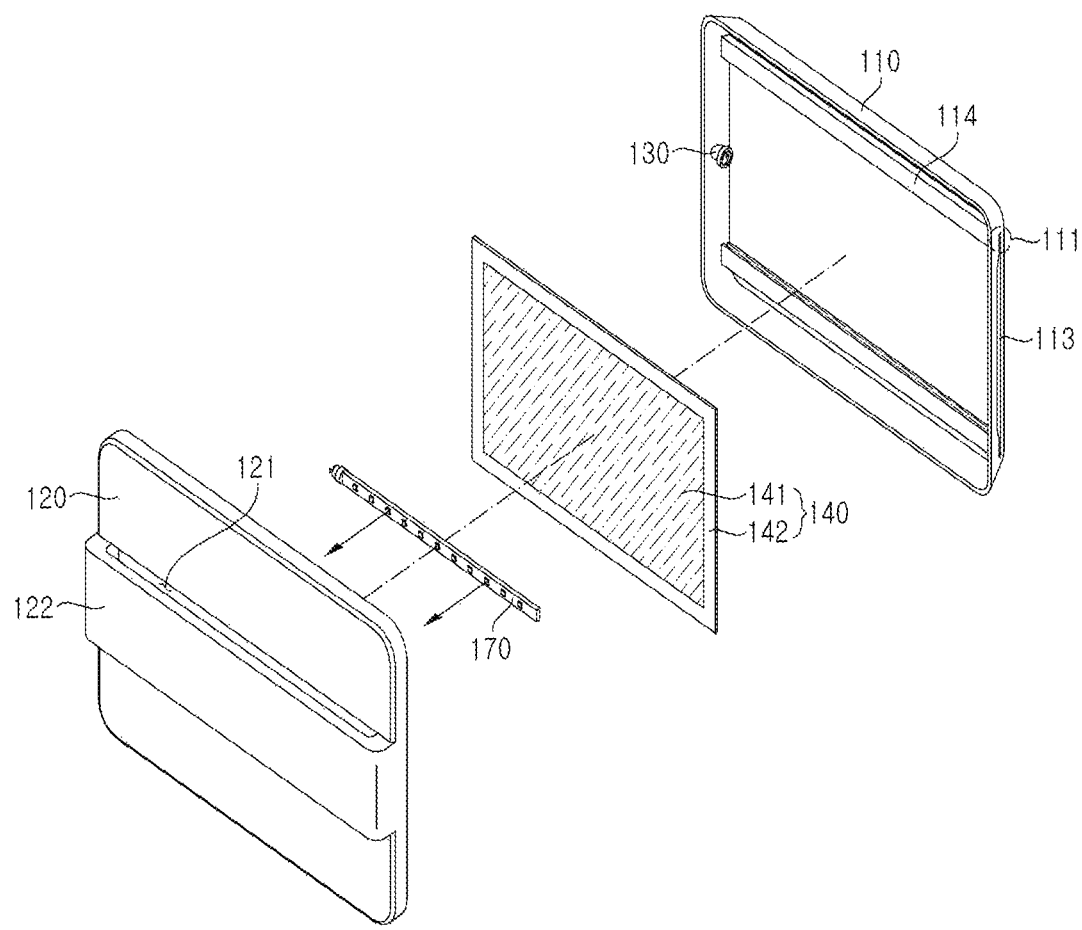
FIG. 24 shows an adhesive-type insect trap having a main body with a guide rail according to an embodiment of the present disclosure.

Referring to FIG. 24, in the adhesive-type insect trap 1000, 2000, 3000, 4000, 5000, 6000, 7000, 8000, 9000, 1100 or 1200, the main body 110 may have a guide rail 114 which guides the adhesive sheet 140, 240, 340, 440, 540 or 640 into the main body 110. The guide rail 114 may guide the adhesive sheet 140, 240, 340, 440, 540 or 640 to be secured inserted into the main body 110 along the guide groove 111 or 211 without being adhered to the main body 110. Further, the guide rail 114 may have a thickness corresponding to a thickness of the adhesive sheet 140, 240, 340, 440, 540 or 640 to allow easy insertion and separation of the adhesive sheet 140, 240, 340, 440, 540 or 640 while receiving an edge of the adhesive sheet 140, 240, 340, 440, 540 or 640 inserted thereinto, and a depth preventing the flypaper piece 141 of the adhesive sheet 140, 240, 340, 440, 540 or 640 from contacting the main body 110.

Figure 25:
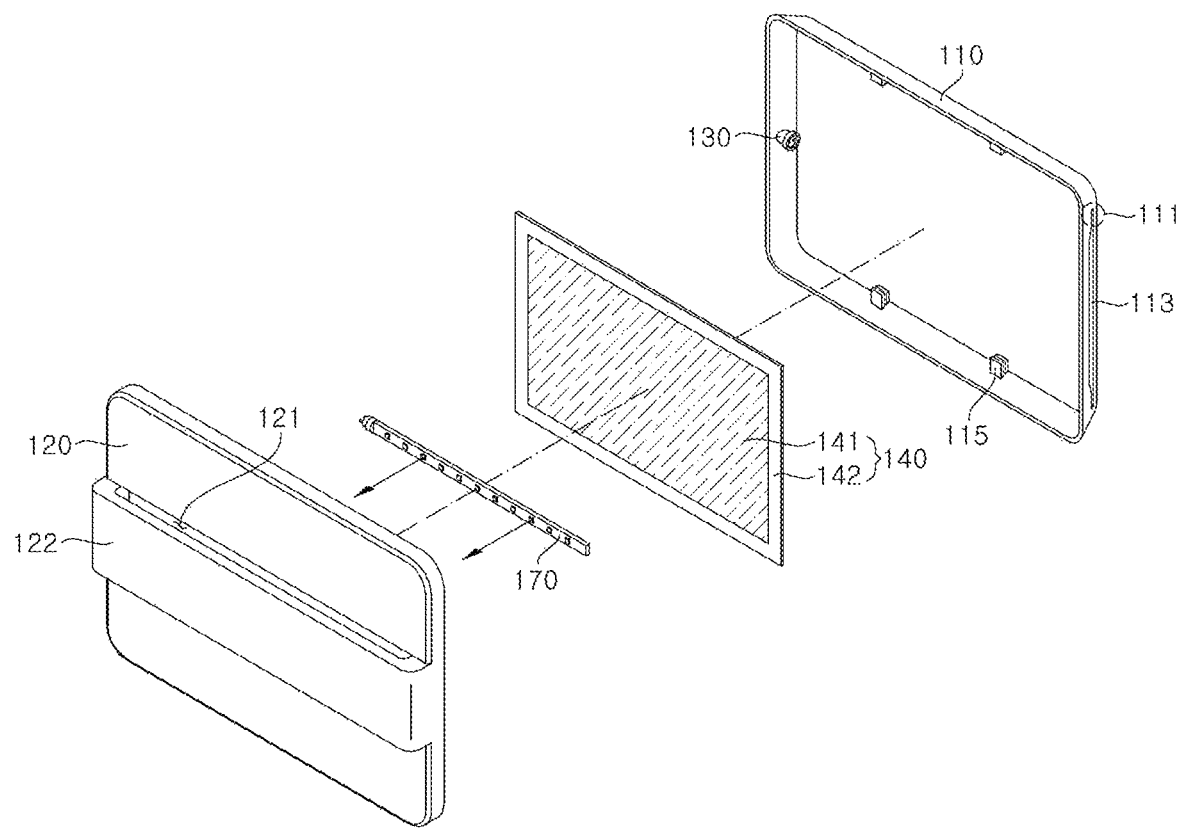
FIG. 25 shows an adhesive-type insect trap having a main body with one exemplary adhesive sheet support according to an embodiment of the present disclosure.
Figure 26:
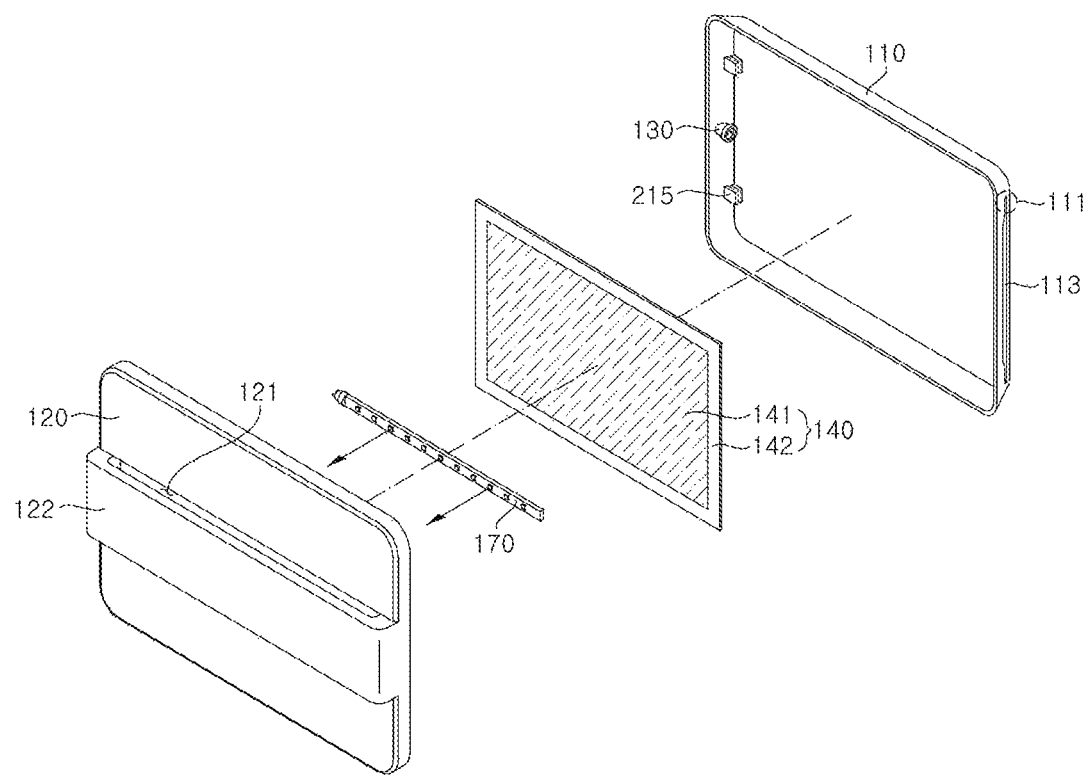
FIG. 26 shows an adhesive-type insect trap having a main body with another exemplary adhesive sheet support according to an embodiment of the present disclosure.

Referring to FIG. 25 and FIG. 26, in the adhesive-type insect trap 1000, 2000, 3000, 4000, 5000, 6000, 7000, 8000, 9000, 1100 or 1200, the main body 110 may include an adhesive sheet support 115 or 215. The adhesive sheet support 115 or 215 may support or secure the adhesive sheet 140, 240, 340, 440, 540 or 640 to prevent the adhesive sheet 140, 240, 340, 440, 540 or 640 inserted into the main body 110 from being adhered to the main body 110.

Figure 27:
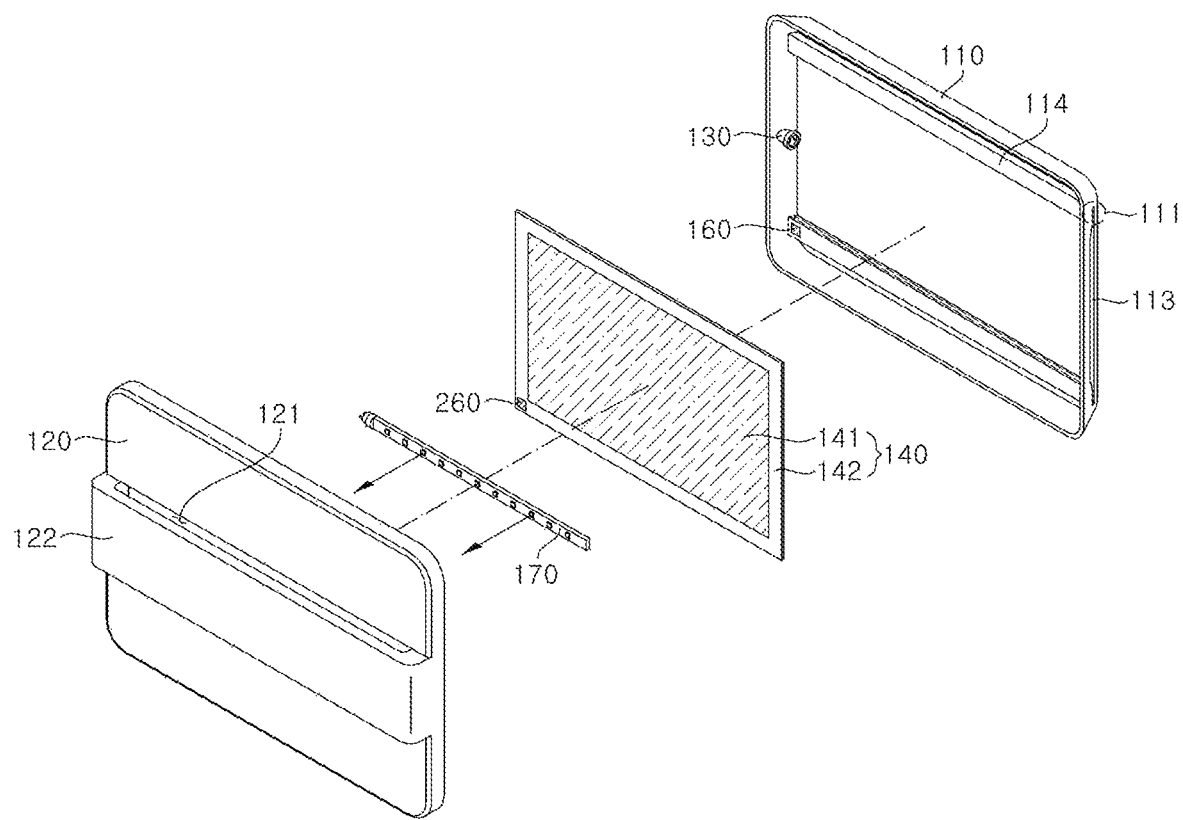
FIG. 27 shows an embodiment of the adhesive-type insect trap having magnet members according to the present disclosure.

Referring to FIG. 27, in the adhesive-type insect trap 1000, 2000, 3000, 4000, 5000, 6000, 7000, 8000, 9000, 1100 or 1200, the guide rail 114 and the adhesive sheet 140, 240, 340, 440, 540 or 640 may include magnet members 160, 260 disposed to face each other and having opposite polarities. That is, the adhesive sheet 140, 240, 340, 440, 540 or 640 are prevented from being separated from the main body even upon rotation of the adhesive-type insect trap 1000, 2000, 3000, 4000, 5000, 6000, 7000, 8000, 9000, 1100 or 1200 according to installation environments by a user after the adhesive sheet 140, 240, 340, 440, 540 or 640 is inserted into the main body 110.

The adhesive-type insect trap 1000, 2000, 3000, 4000, 5000, 6000, 7000, 8000, 9000, 1100 or 1200 may further include a photocatalyst. For example, the photocatalyst may be coated or attached to the rear side of the cover 120, the front side or the lateral side of the main body 110, the reflector 150 or 250, and the adhesive sheet 140, 240, 340 or 440. Alternatively, a separate photocatalyst filter may be mounted on the adhesive-type insect traps.

The photocatalyst may include photocatalyst media generating photocatalytic reaction. For example, the photocatalyst media may include titanium oxide ($TiO_2$), silicon oxide ($SiO_2$), tungsten oxide ($WO_3$), zirconium oxide (ZnO), strontium titanium oxide ($SrTiO_3$), niobium oxide ($Nb_2O_5$), iron oxide ($Fe_2O_3$), zinc oxide ($ZnO_2$), tin oxide ($SnO_2$), and the like.

In addition, hydroxyl radicals generated by photocatalytic reaction of the photocatalyst act as a strong oxidant, which performs a sterilization function, and decomposes contaminants and odorous substances in air, which has flown into the adhesive-type insect trap 1000, 2000, 3000, 4000, 5000, 6000, 7000, 8000, 9000, 1100 or 1200, into water and carbon dioxide by decomposing organic contaminants in air through oxidation. Here, carbon dioxide is known as a substance having an effect of attracting mosquitoes.

As such, the adhesive-type insect trap 1000, 2000, 3000, 4000, 5000, 6000, 7000, 8000, 9000, 1100 or 1200 further include the photocatalyst to provide not only sterilization and deodorization effects, but also an effect of attracting insects, particularly mosquitoes, through generation of carbon dioxide during photocatalytic reaction.

The adhesive-type insect trap 1000, 2000, 3000, 4000, 5000, 6000, 7000, 8000, 9000, 1100 or 1200 may further include a switch (not shown) for controlling a power supply system of the light source mount 130. Here, a power supply may be disposed at any location without being limited to a particular location.

In addition, the adhesive-type insect trap 1000, 2000, 3000, 4000, 5000, 6000, 7000, 8000, 9000, 1100 or 1200 may include a camera to allow a user to observe insects trapped on the adhesive sheet 140, 240, 340 or 440. The camera may have a zoom function, whereby a user can move the camera or use the zoom function at a remote location through transmission of a signal to a communication module mounted on the adhesive-type insect trap 1000, 2000, 3000, 4000, 5000, 6000, 7000, 8000, 9000, 1100 or 1200 when photographing insects trapped in the adhesive-type insect trap 1000, 2000, 3000, 4000, 5000, 6000, 7000, 8000, 9000, 1100 or 1200.

Further, the adhesive-type insect trap 1000, 2000, 3000, 4000, 5000, 6000, 7000, 8000, 9000, 1100 or 1200 may include a sensor to allow a user to ascertain the presence of insects trapped in the insect trap or to ascertain an area of the adhesive sheet 140, 240, 340 or 440 occupied by insects trapped thereon, and may perform a notification function to a user through the communication module when the sensor detects that insects are trapped or that the area of the adhesive sheet occupied by insects trapped thereon exceeds a preset value. By way of example, the sensor may include a brightness sensor for detecting brightness of the adhesive sheet 140, 240, 340 or 440. The brightness sensor may detect a collected amount of insects through brightness comparison between a region to which insects are attached and a region to which no insects are attached.

Further, the adhesive-type insect trap 1000, 2000, 3000, 4000, 5000, 6000, 7000, 8000, 9000, 1100 or 1200 may include an insect attractant spray (not shown) or may include an insect attractant contained in an adhesive sheet to improve insect attraction efficiency.

Further, the adhesive-type insect trap 1000, 2000, 3000, 4000, 5000, 6000, 7000, 8000, 9000, 1100 or 1200 may include a light diffusion material applied to or coated on the adhesive sheet 140, 240, 340 or 440 to diffuse light emitted from the light source 170, 270, 370, 470, 570, 670 or 770, thereby improving efficiency in attraction of insects, particularly flies.

Insects, particularly flies, tend to be more strongly attracted to refracted or diffused light than to direct light. The adhesive-type insect trap 1000, 2000, 3000, 4000, 5000, 6000, 7000, 8000, 9000, 1100 or 1200 can refract or diffuse light from the light source 170, 270, 370, 470, 570, 670 or 770, thereby improving efficiency in attraction of insects with decoy light.

In this point of view, a light refracting portion according to the present disclosure may include a light refracting agent 123, a light refracting agent film 124, and a roughness portion 125 or 225. FIG. 28 to FIG. 37 shows embodiments of arrangement of the cover 120, 220 or 320, the light source 170, 270, 370, 470, 570, 670 or 770, and the light refracting portion 123, 124 or 125, and it should be understood that the structure of the adhesive-type insect trap according to the present disclosure is not limited to the description and the accompanying drawings of the specification.

By way of example, the light refracting agent 123 may be a mixture of a light scattering powder and a solvent, and may be a material obtained before or after curing the mixture. The light refracting agent film 124 refers to a film formed by curing the light refracting agent 123. For example, the light refracting agent 123 may include at least one selected from among titanium dioxide ($TiO_2$), calcium carbonate ($CaCO_3$) and calcium phosphate ($Ca_3(PO_4)_2$), which causes light scattering upon impact with light emitted from the light source 170, 270, 370, 470, 570, 670 or 770. For example, the light refracting agent 123 may be implemented by a mixture of at least one powder having a diameter of 0.01 mm to 0.1 mm and selected from among at least titanium dioxide ($TiO_2$), calcium carbonate ($CaCO_3$) and calcium phosphate ($Ca_3(PO_4)_2$) and a solvent, or a cured product of the mixture. For example, the solvent may be a curable solvent and may include at least one selected from among an organic solvent, an aqueous polyvinyl alcohol solution, liquid silicone, and a transparent epoxy resin. Here, the liquid silicone or the transparent epoxy resin may be a transparent or translucent resin. The translucent resin can further improve optical effects for light refraction, as compared to the transparent resin. That is, the cover 120, 220 or 320 includes the light refracting agent 123, which can scatter light emitted from the light source 170, 270, 370, 470, 570, 670 or 770, thereby further improving insect trapping efficiency through improvement in insect attraction efficiency of light.

Figure 28:
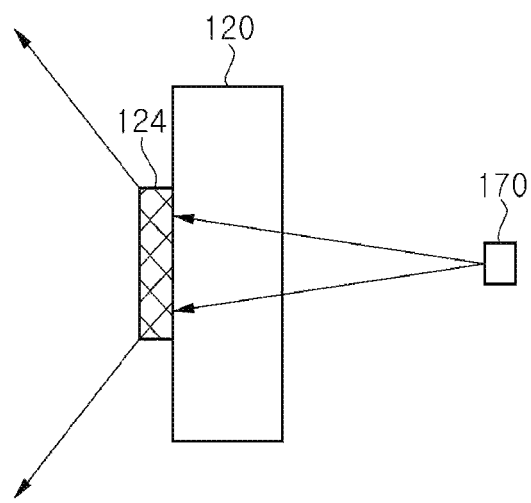
FIG. 28 shows one embodiment of arrangement of a cover, a light source and a light refracting portion according to the present disclosure.
Figure 29:
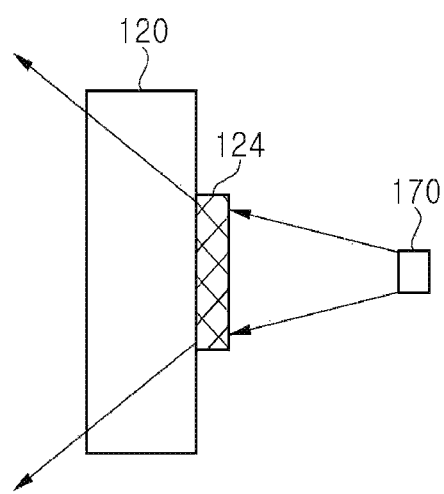
FIG. 29 shows another embodiment of arrangement of a cover, a light source and a light refracting portion according to the present disclosure.
Figure 30:
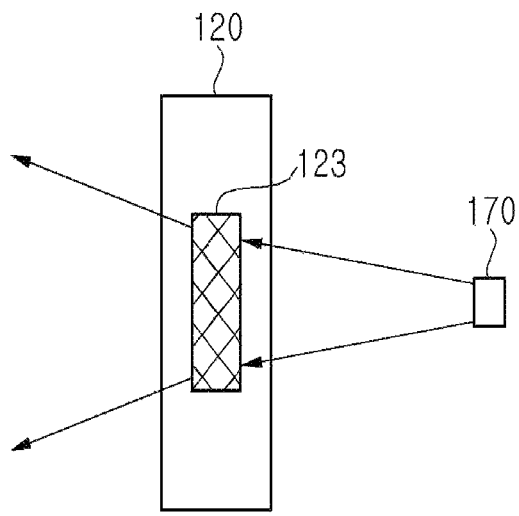
FIG. 30 shows further another embodiment of arrangement of a cover, a light source and a light refracting portion according to the present disclosure.

By way of example, in the adhesive-type insect trap according to the present disclosure, the cover 120, 220 or 320 may include the light refracting agent 123 on a surface thereof, as shown in FIG. 28 to FIG. 29, or may include the light refracting agent 123 therein, as shown in FIG. 30. The light refracting agent 123 may be realized by a form in which at least one of titanium dioxide ($TiO_2$), calcium carbonate ($CaCO_3$) and calcium phosphate ($Ca_3(PO_4)_2$) is applied in powder form to the cover 120, 220 or 320 or by the light refracting agent film 124 in which at least one of titanium dioxide ($TiO_2$), calcium carbonate ($CaCO_3$) and calcium phosphate ($Ca_3(PO_4)_2$) is attached in powder form to the cover 120, 220 or 320. Here, the surface of the cover 120, 220 or 320 includes an outer surface and an inner surface thereof. Here, the inner surface of the cover 120, 220 or 320 refers to a surface disposed proximate the light source 170, 270, 370, 470, 570, 670 or 770 and the outer surface of the cover 120, 220 or 320 refers to a surface relatively distal from the light source 170, 270, 370, 470, 570, 670 or 770. For example, the light source and the cover may be disposed to allow light emitted from the light source 170, 270, 370, 470, 570, 670 or 770 to pass through the inner surface of the cover 120, 220 or 320 and then through the outer surface of the cover 120, 220 or 320.

By way of example, as shown in FIG. 28 to FIG. 29, the light refracting portion may be implemented by the light refracting agent film 124 formed by attaching the light refracting agent 123 to the surface of the cover 120, 220 or 320. The light refracting agent film 124 may be implemented by a cured product of the mixture of the light refracting agent 123 and the solvent or by curing the mixture deposited on a transparent substrate (not shown). That is, the cover 120, 220 or 320 may include a light refraction film attached to the outer or inner surface of the cover 120, 220 or 320 to refract light emitted from the light source 170, 270, 370, 470, 570, 670 or 770, thereby further improving insect trapping efficiency through improvement in insect attraction efficiency of light.

By way of example, as shown in FIG. 30, the light refracting portion may be implemented by the light refracting agent 123 placed inside the cover 120, 220 or 320. The light refracting agent 123 may be formed to be placed inside the cover 120, 220 or 320 upon molding of the cover 120, 220 or 320. To this end, the cover 120, 220 or 320 may be provided with a pouring inlet, through which the light refracting agent 123 is poured, and the light refracting portion may be formed by pouring the light refracting agent 123 into the cover 120, 220 or 320 after manufacture of the cover 120, 220 or 320, followed by curing the light refracting agent. That is, the cover 120, 220 or 320 includes the light refracting agent 123 therein to refract light emitted from the light source 170, 270, 370, 470, 570, 670 or 770, thereby further improving insect trapping efficiency through improvement in insect attraction efficiency of light.

Figure 31:
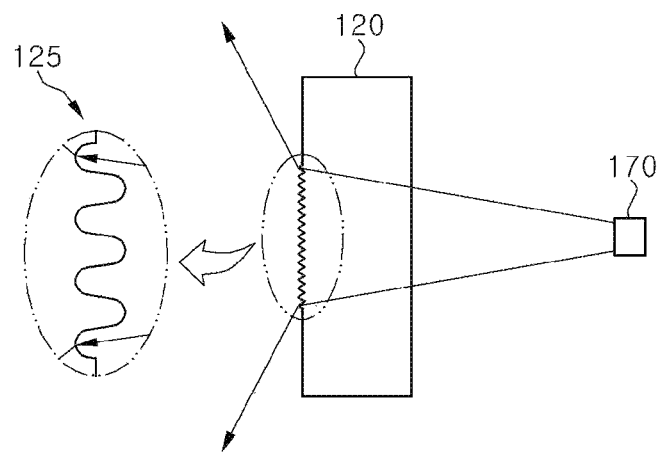
FIG. 31 shows one embodiment of a light refracting portion having a roughness portion according to the present disclosure.
Figure 32:
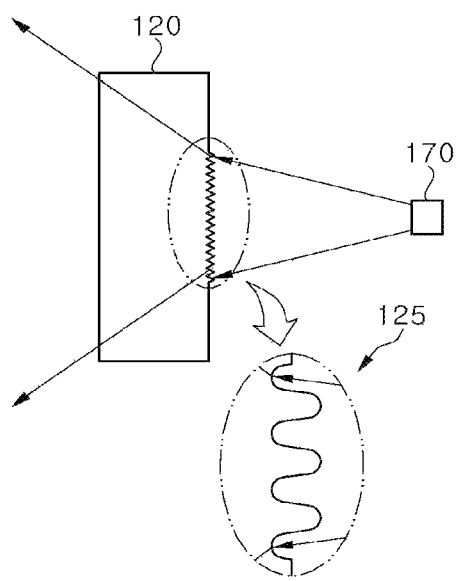
FIG. 32 shows another embodiment of a light refracting portion having a roughness portion according to the present disclosure.

By way of example, the light refracting portion may include the roughness portion 125 as shown in FIG. 31. The roughness portion 125 may be formed on the outer surface of the cover 120, 220 or 320, as shown in FIG. 31, or may be formed on the inner surface of the cover 120, 220 or 320, as shown in FIG. 32. The roughness portion 125 may be formed by performing alumite treatment, unsealed alumite treatment, acid etching treatment, zinc plating chromate treatment, sand blasting, and the like on the surface of the cover 120, 220 or 320. As shown in FIG. 32, the roughness portion 125 includes a convex portion and a concave portion such that light emitted from the light source 170, 270, 370, 470, 570, 670 or 770 can be refracted while passing through the convex portion and the concave portion. That is, the cover 120, 220 or 320 includes the roughness portion 125 formed on the surface thereof to refract light emitted from the light source 170, 270, 370, 470, 570, 670 or 770, thereby further improving insect trapping efficiency through improvement in insect attraction efficiency of light.

Figure 33:
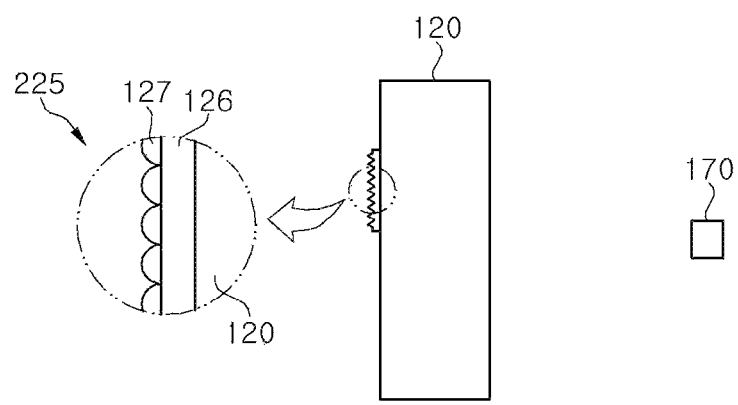
FIG. 33 shows further another embodiment of arrangement of a light refracting portion having a roughness portion according to the present disclosure.
Figure 34:
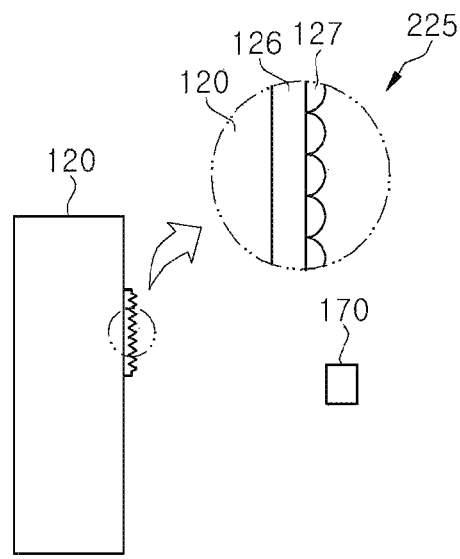
FIG. 34 shows further another embodiment of arrangement of a light refracting portion having a roughness portion according to the present disclosure.
Figure 35:
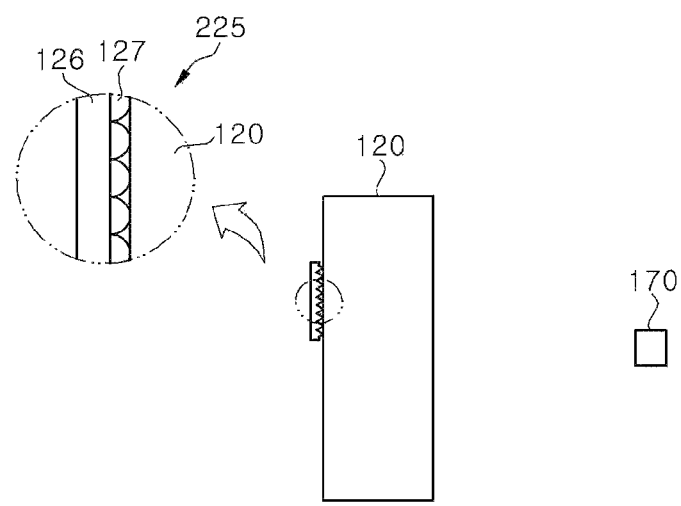
FIG. 35 shows another embodiment of a light refracting portion having a different roughness portion according to the present disclosure.
Figure 36:
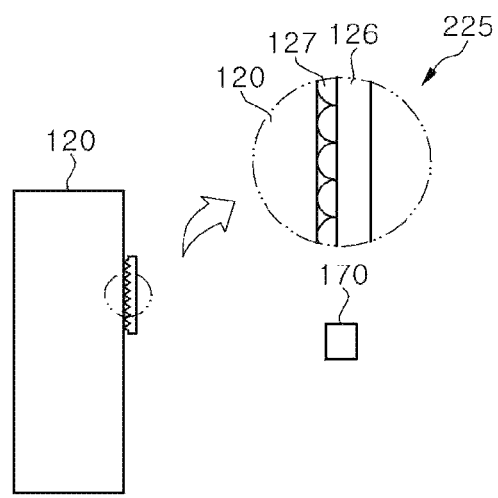
FIG. 36 shows yet another embodiment of a light refracting portion having a different roughness portion according to the present disclosure.

By way of example, as shown in FIG. 33 to FIG. 36, the light refracting portion may include the roughness portion 225, which may include a base 126 and protrusions 127. FIG. 31 to FIG. 32 show an embodiment wherein the light refracting portion includes the roughness portion 225 directly formed on the cover 120, 220 or 320, and FIG. 33 to FIG. 36 show an embodiment wherein the light refracting portion includes the roughness portion 225 attached to the surface of the cover 120, 220 or 320 and including the base 126 and the protrusions 127. The base 126 and the roughness portion 225 may be formed of a transparent or translucent material, for example, the same material as the cover 120, 220 or 320. For example, the roughness portion 225 may have a structure wherein the base 126 is attached to the surface of the cover 120, 220 or 320, as shown in FIG. 33 and FIG. 34, or a structure wherein the protrusions 127 are attached to the surface of the cover 120, 220 or 320, as shown in FIG. 35 and FIG. 36. That is, the cover 120, 220 or 320 includes the roughness portion 225 attached to the surface of the cover 120, 220 or 320 to refract light emitted from the light source 170, 270, 370, 470, 570, 670 or 770, thereby further improving insect trapping efficiency through improvement in insect attraction efficiency of light.

Figure 37:
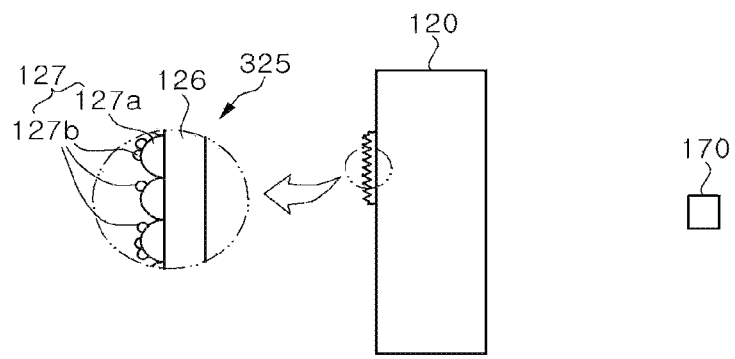
FIG. 37 shows yet another embodiment of arrangement of a light refracting portion having a different roughness portion according to the present disclosure.

By way of example, as shown in FIG. 37, a roughness portion 325 includes a base 126 and protrusions 127, which may include a first protrusion 127a and a second protrusion 127b attached to the first protrusion 127a. Here, the first protrusion 127a and the second protrusion 127b may be formed to have different volumes, thereby further improving efficiency in refraction of light emitted from the light source 170, 270, 370, 470, 570, 670 or 770. For example, the base 126 may be attached to the surface of the cover 120, 220 or 320, the first protrusion 127a may be formed on the base 126, and one or more second protrusions 127b having a smaller volume than the first protrusion 127a may be attached to the first protrusion 127a. That is, the cover 120, 220 or 320 may include the roughness portion 325 attached to the surface of the cover 120, 220 or 320 and including at least two protrusions 127 having different volumes to further improve efficiency in refraction of light emitted from the light source 170, 270, 370, 470, 570, 670 or 770, thereby further improving insect trapping efficiency through improvement in insect attraction efficiency of light.

In an alternative embodiment different from the embodiments described with reference to FIG. 28 to FIG. 37, the reflector 150 or 250 as shown in FIGS. 6, 8 and 9 may have a roughened surface, may include a separate diffusion film attached thereto or coated thereon, or may include a diffusion agent applied thereto or coated thereon. Alternatively, the light source 170, 270, 370, 470, 570, 670 or 770 may have a roughened surface, may include a separate diffusion film attached thereto or coated thereon, or may include a diffusion agent applied thereto or coated thereon. For example, the case 174 of the light source 770 shown in FIG. 17 may have a roughened surface, may include a separate diffusion film attached thereto or coated thereon, or may include a diffusion agent applied thereto or coated thereon.

FIG. 38 to FIG. 44 show a method of coupling a cover to a main body of an adhesive-type insect trap according to one embodiment of the present disclosure. For coupling between a main body 410 and a cover 420, a latch coupling mechanism and/or combination of the latch coupling mechanism and an additional coupling mechanism using physical force such as magnetic force may be used.

For example, the main body 410 may be coupled to the cover 420 through a first coupling means using a latch coupling mechanism between a coupling portion and a receiving portion. Alternatively, the main body 410 may be coupled to the cover 420 not only by the latch coupling mechanism such as the first coupling means, but also a second coupling means using an additional coupling mechanism such as magnetic force.

The first coupling means may include, for example, a coupling mechanism in which a first coupling portion 421 and a first receiving portion 411 are coupled to each other through latch coupling. Here, the first coupling portion 421 may be provided to the cover 420, which has a smaller volume and weight than the main body 410 to allow easy movement control, and the first receiving portion 411 may be provided to the main body 410. However, it should be understood that the present disclosure is not limited thereto and the locations of the first coupling portion and the first receiving portion may be switched.

Figure 38:
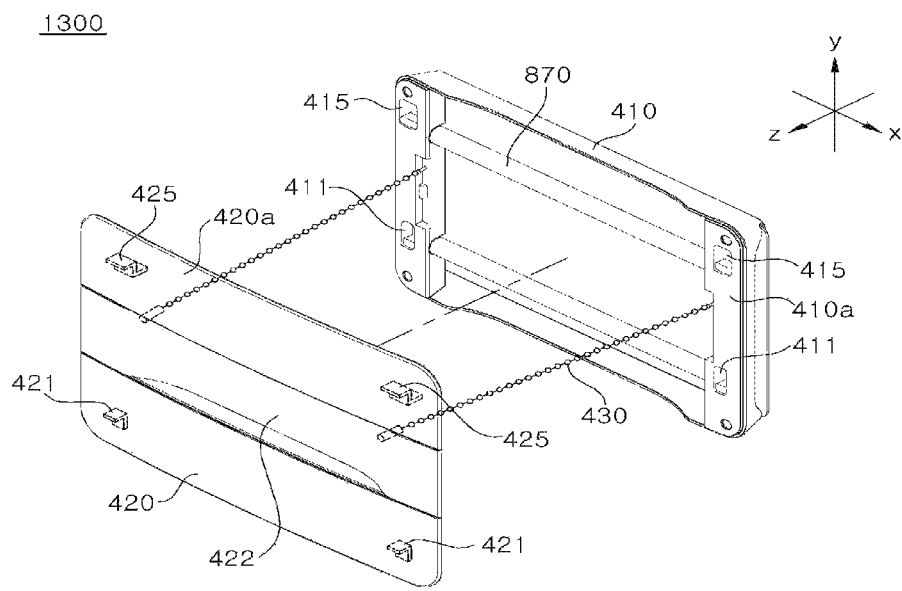
FIG. 38 shows an embodiment of method of coupling a cover to a main body of an adhesive-type insect trap with at least one first coupling portion according to the present disclosure.

Referring to FIG. 38, a cover inner surface 420a may include at least one first coupling portion 421. Here, the cover inner surface 420a may refer to a surface of the cover facing the main body 410 when the cover 420 is coupled to the main body 410. Although the cover 420 is transparently shown in FIG. 38 to show the first coupling portion 421, transparency of the cover 420 is not particularly limited.

Figure 39:
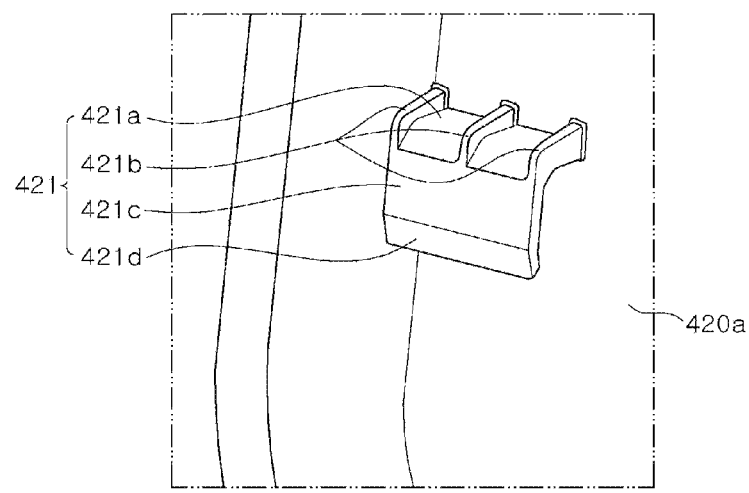
FIG. 39 shows an enlarged view of the first coupling portion of the cover as shown in FIG. 38.

FIG. 39 is an enlarged view of the first coupling portion 421 of the cover 420. The first coupling portion 421 may include a support portion and a hook portion. Referring to FIG. 39, the first coupling portion 421 includes a first support portion 421a and a first hook portion 421c. The first support portion 421a may have a thin plate shape extending substantially perpendicularly from the inner surface 420a of the cover 420. The first support portion 421a may further include first assistant support portions 421b to increase coupling force to the cover inner surface 420a and force of supporting the first hook portion 421c. The first assistant support portions 421b may protrude from the first support portion 421a. For example, the first assistant support portions 421b may have a plate shape perpendicular not only to the cover inner surface 420a but also to the first support portion 421a. Referring to FIG. 39, three first assistant support portions 421b are disposed on the first support portion 421a of the first coupling portion 421 to be separated from each other. The first assistant support portions 421b can prevent the first support portion 421a from being damaged by physical force that can be applied upwards or downwards upon coupling and separation of the cover 420.

The first hook portion 421c may extend from one end of the first support portion 421a so as to be substantially horizontal to the cover inner surface 420a. The first hook portion 421c may have a plate shape substantially perpendicular to the first support portion 421a. Here, a distal end 421d of the first hook portion may be bent towards the cover inner surface 420a. Further, the distal end 421d of the first hook portion may have a greater thickness than other portions of the first hook portion 421c. With this structure, coupling force between the first coupling portion 421 and the first receiving portion 411 can be increased.

Figure 40:
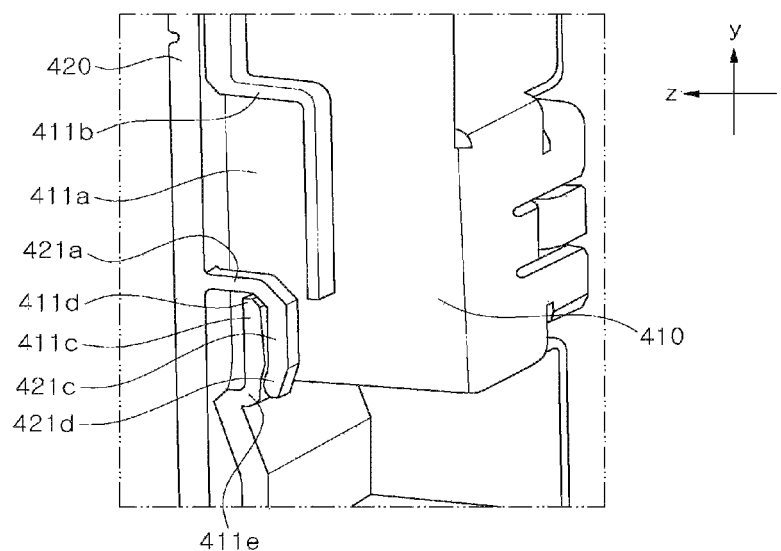
FIG. 40 is a perspective view of coupling between the first coupling portion of the cover and a first receiving portion according to the present disclosure.
Figure 41:
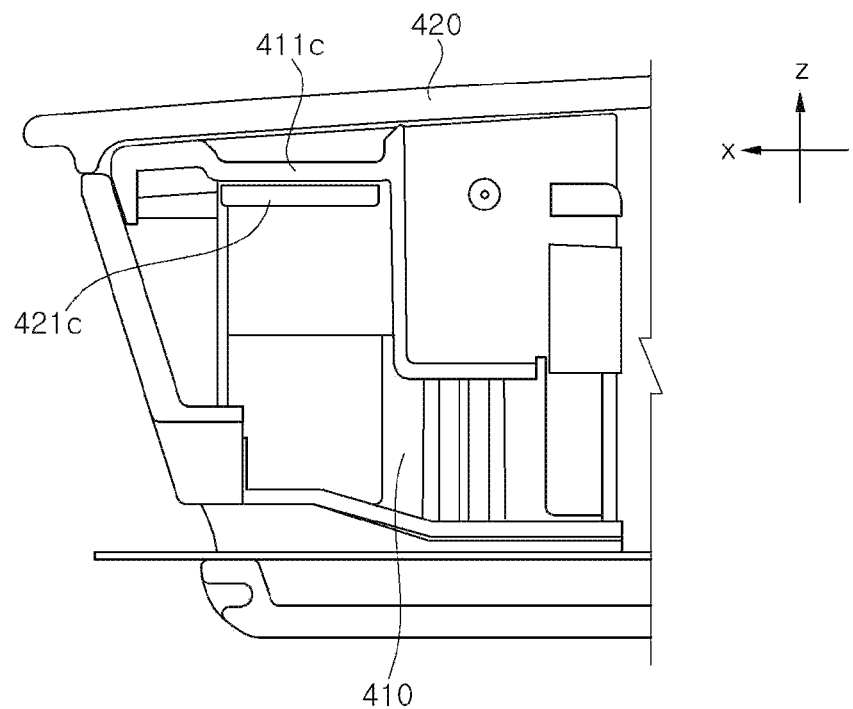
FIG. 41 is a cross sectional view of coupling between the first coupling portion of the cover and a first receiving portion.

FIG. 40 and FIG. 41 are cross-sectional views illustrating coupling between the first coupling portion 421 of the cover 420 and the first receiving portion 411 disposed on the front surface 410a of the main body. Here, the front surface 410a of the main body means a surface of the main body facing the cover 420 upon coupling between the main body 410 and the cover 420. Specifically, FIG. 40 is a cross-sectional view of a coupled structure between the first coupling portion 421 and the first receiving portion 411 taken in a y-z plane and FIG. 41 is a cross-sectional view of the coupled structure taken in an x-z plane.

The first receiving portion 411 may include a first groove 411a, a first guide portion 411b, and a first catch portion 411c. Referring to FIG. 38 and FIG. 40, two first grooves 411a are disposed at a lower portion of the front surface 410a of the main body. The first guide portion 411b is disposed at an upper side of the first groove 411a to guide insertion of the first coupling portion 421 and the first catch portion 411c is disposed at a lower side of the first groove 411a. Upon coupling between the cover 420 and the main body 410, the first hook portion 421c of the first coupling portion 421 may be placed on the first catch portion 411c of the first receiving portion 411 to be caught thereby.

Upon coupling of the cover 420 to the main body 410, the first coupling portion 421 protruding from the cover 420 is inserted into the first groove 411a along the first guide portion 411b of the first receiving portion 411, whereby the cover inner surface 420a can be brought into close contact with the front surface 410a of the main body. After the first coupling portion 421 is completely inserted into the first groove 411a along the first guide portion 411b of the first receiving portion 411, the first coupling portion 421 is moved downwards along the first guide portion 411b to allow the first hook portion 421c of the first receiving portion 411 to be caught by the first catch portion 411c. Upon coupling, the first support portion 421a of the first coupling portion 421 is brought into contact with the distal end 411d of the first catch portion of the first receiving portion 411 to define a location, that is, a height, at which the cover 420 is coupled to the main body 410. Further, the first hook portion 421c of the first coupling portion 421 is caught by the first catch portion 411c of the first receiving portion 411 to prevent the cover 420 from being separated or moved from a direction towards the front surface of the main body 410. A lower end 411e of the first catch portion of the first receiving portion 411 may have a smaller thickness than other portions thereof. This structure is provided for the purpose of increasing coupling force, corresponding to the structure wherein the distal end 421d of the first hook portion of the first coupling portion 421 is bent and has a great thickness, as described above.

A separation distance between the first hook portion 421c of the first coupling portion 421 and the cover inner surface 420a may be significantly large, as compared to the thickness of the first catch portion 411c of the first receiving portion 411. As a result, a spatial margin is provided upon coupling of the first coupling portion 421 to the first receiving portion 411, thereby enabling relatively easy coupling or separation between the cover 420 and the main body 410.

The second coupling means includes, for example, coupling between the second coupling portion 425 and the second receiving portion 415 through the latch coupling mechanism and an additional coupling mechanism. For example, the second coupling means may include not only the latch coupling mechanism, but also an additional coupling mechanism such as magnetic force.

As shown in FIG. 38, the second coupling portion 425 may be provided to the cover 420, which has a smaller volume and weight than the main body 410 to allow easy movement control, and the second receiving portion 415 may be provided to the main body 410. However, it should be understood that the present disclosure is not limited thereto and the locations of the second coupling portion 425 and the second receiving portion may be switched.

Figure 42:
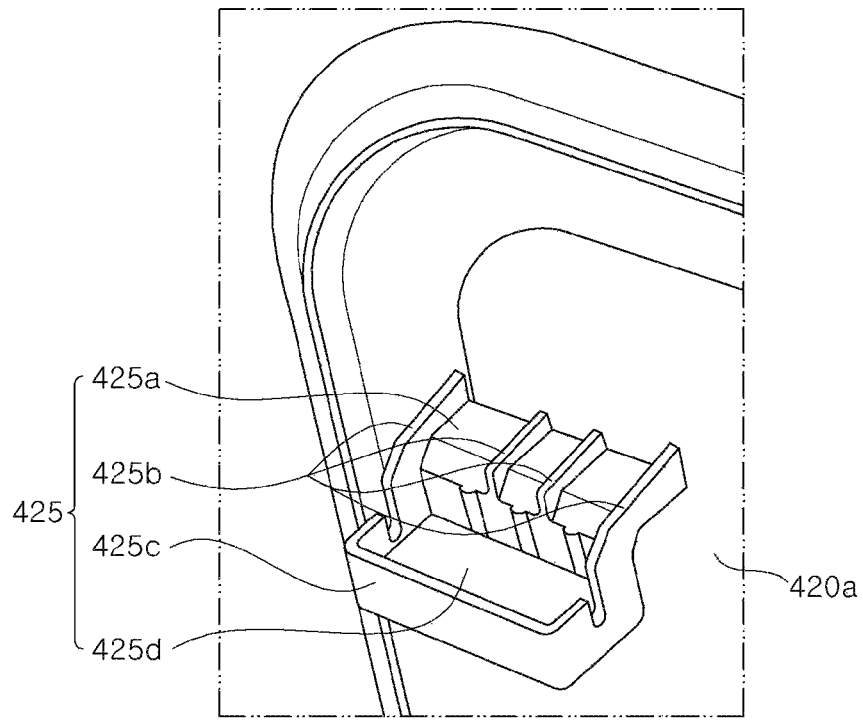
FIG. 42 shows an enlarged view of a second coupling portion of the cover according to one embodiment of the present disclosure.

FIG. 42 is an enlarged view of the second coupling portion 425 of the cover. Like the first coupling portion 421, the second coupling portion 425 may include a support portion and a hook portion. Referring to FIG. 42, the second coupling portion 425 includes a second support portion 425a and a second hook portion 425c. The second support portion 425a may have a similar shape to the first support portion 421a. That is, the second support portion 425a may have a thin plate shape extending substantially perpendicularly from the cover inner surface 420a and may further include a plurality of second assistant support portions 425b. The second assistant support portions 425b may protrude from the second support portion 425a. Referring to FIG. 42, four second assistant support portions 425b are disposed on the second support portion 425a of the second coupling portion 425 to be separated from each other. The second assistant support portions 425b can prevent the second support portion 425a from being damaged by physical force that can be applied upwards or downwards upon coupling and separation of the cover 420. As described below, since the second hook portion 425c of the second coupling portion 425 includes a magnet member and thus has a relatively large weight, the second support portion 425a may include more second assistant support portions 425b than the first support portion 421a.

The second hook portion 425c may extend from one end of the second support portion 425a to be substantially perpendicular to the second support portion 425a. To increase coupling force between the second coupling portion 425 and the second receiving portion 415, the second hook portion 425c may be separated from the cover inner surface 420a and may include an empty space having a particular size to receive the magnet member 425d generating magnetic force having a particular magnitude or more in the empty space. The empty space of the second hook portion 425c is open at an upper portion thereof, thereby enabling easy replacement of the magnet member 425d when the magnetic force of the magnet member decreases.

Figure 43:
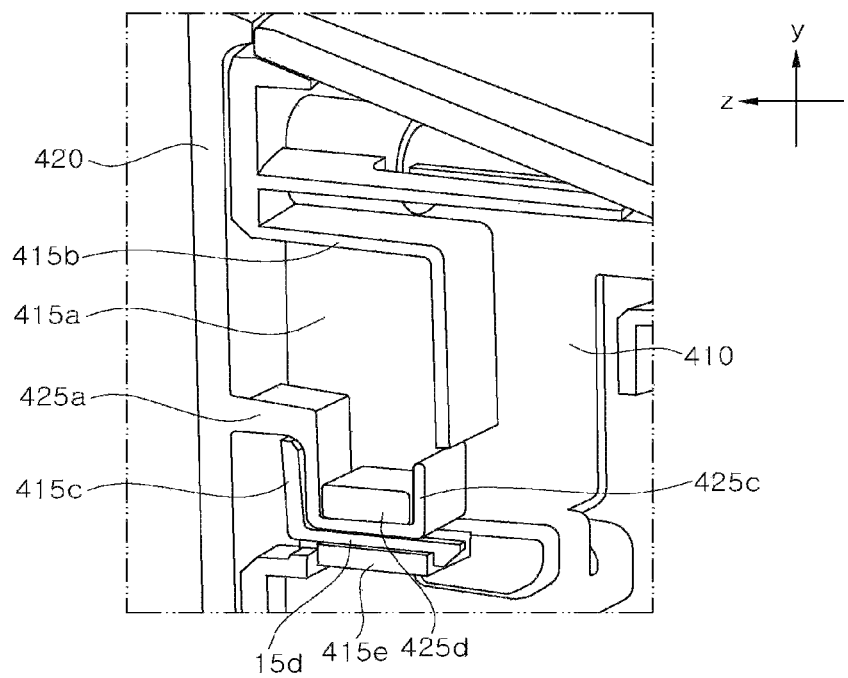
FIG. 43 shows a perspective view of coupling between the second portion of the cover and a second receiving portion.
Figure 44:
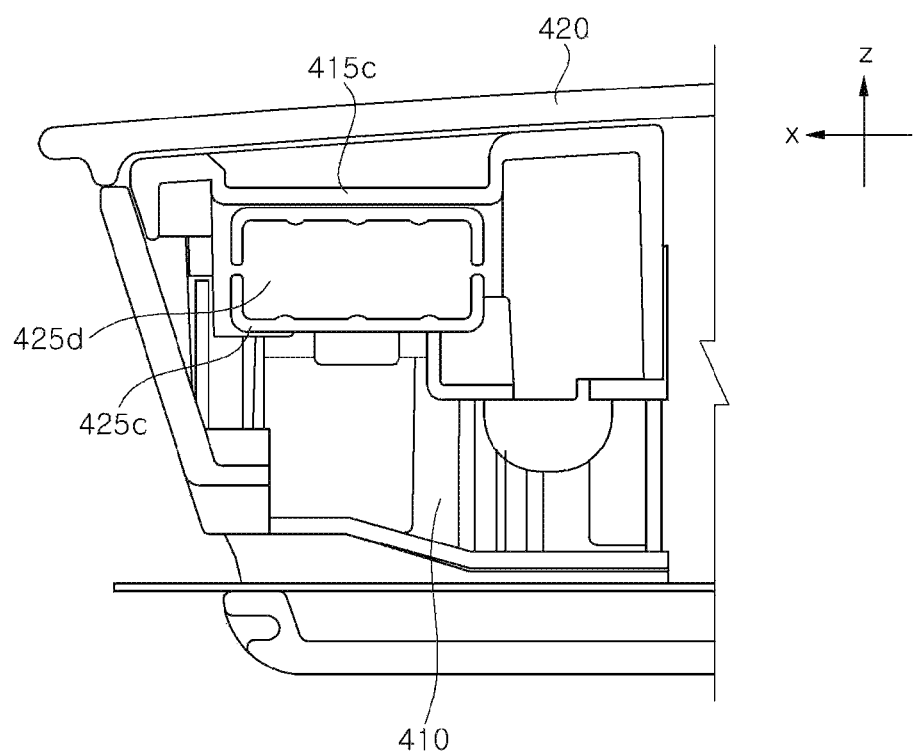
FIG. 44 is a cross sectional view of the coupling as shown in FIG. 43.

FIG. 43 and FIG. 44 are cross-sectional views illustrating coupling between the second coupling portion 425 of the cover and the second receiving portion 415 disposed on the front surface of the main body. Specifically, FIG. 43 is a cross-sectional view of a coupled structure between the second coupling portion 425 and the second receiving portion 415 taken in a y-z plane and FIG. 44 is a cross-sectional view of the coupled structure taken in an x-z plane.

The second receiving portion 415 may include a second groove 415a; a second guide portion 415b, a second catch portion 415c, and a rack 415d disposed in the second groove 415a; and a magnetic coupling portion 415e disposed under the rack 415d. Referring to FIG. 38 and FIG. 32, two second grooves 415a are disposed at an upper side of the front surface 410a of the main body. The second guide portion 415b is disposed at an upper portion of each of the second grooves 415a to guide insertion of the second coupling portion 425, and the second catch portion 415c, the rack 415d and the magnetic coupling portion 415e are disposed at a lower portion of the second groove 415a. Upon coupling between the cover 420 and the main body 410, the second hook portion 425c of the second coupling portion 425 may be placed on the second catch portion 415c of the second receiving portion 415 to be caught thereby. Upon coupling of the cover 420 to the main body 410, the second coupling portion 425 protruding from the cover 420 is inserted into the second groove 415a along the second guide portion 415b of the second receiving portion 415, whereby the cover inner surface 420a can be brought into close contact with the front surface 410a of the main body without being separated therefrom. After the second coupling portion 425 is completely inserted into the second groove 415a along the second guide portion 415a of the second receiving portion 415, the second coupling portion 425 is moved downwards along the second guide portion 415a to allow the second hook portion 425c of the second coupling portion 425 to be caught by the second catch portion 415c of the second receiving portion 415. Upon coupling, the second hook portion 425c of the second coupling portion 425 is brought into contact with the rack 415d of the second receiving portion 415 to define a location, that is, a height, at which the cover 420 is coupled to the main body 410. With this latch coupling mechanism, the cover 420 can be prevented from being separated forwards from the main body 410.

The second coupling means can increase coupling force between the cover 420 and the main body 410 using not only the latch coupling mechanism but also magnetic force of the magnet member 425d included in the hook portion. When the second hook portion 425c of the second coupling portion 425 is brought into contact with the rack 415d of the second receiving portion 415, the magnet member 425d disposed in the second hook portion 425c may be coupled to the magnetic coupling portion 415e through magnetic force. Here, the magnetic coupling portion 415e may include a magnet or a metal such as iron, which responds to magnetic force. When the magnetic coupling portion includes a magnet, the magnet may be disposed to exhibit a different polarity from the magnet member 425d provided to the second catch portion 425c. With the coupling mechanism using magnetic force, the cover 420 can be prevented from being separated from the main body 410.

A separation distance between the second hook portion 425c of the second coupling portion 425 and the cover inner surface 420a may be significantly large, as compared to the thickness of the second catch portion 415c of the second receiving portion 415. As a result, a spatial margin is provided upon coupling of the second coupling portion 425 to the second receiving portion 415, thereby enabling relatively easy coupling or separation between the cover 420 and the main body 410.

It should be understood that the additional coupling mechanism of the second coupling means may include not only the use of magnetic force, but also any other mechanism for increasing coupling force between the second coupling portion 425 and the second receiving portion 415. For example, the second coupling means may use a friction means (not shown) to increase coupling force of the second coupling portion 425 to the second receiving portion 415. The friction means may be provided to a surface of the second coupling portion 425 directly adjoining the second receiving portion 415 to increase coupling force therebetween. For example, the friction means may be provided to the second hook portion 425c of the second coupling portion 425 and/or the second catch portion 415c of the second receiving portion 415. Alternatively, the second coupling means may use a bonding means (not shown) to increase coupling force between the second coupling portion 425 and the second receiving portion 415. The bonding means is provided to a lower surface of the second hook portion 425c or to an upper surface of the rack 415e to increase coupling force between the second coupling portion 425 and the second receiving portion 415.

Referring again to FIG. 38, the cover 420 is coupled to the main body 410 through both the first coupling means and the second coupling means. Referring to FIG. 38, the first coupling portion 421 may be disposed at a lower portion of the cover inner surface 420a and the second coupling portion 425 may be disposed at an upper portion of the cover inner surface 420a. Two first coupling portions 421 are disposed at the lower portion of the cover inner surface 420a to be separated from each other with reference to a through-hole blocking structure 422, and two second coupling portion 425 are disposed at the upper portion of the cover inner surface 420a to be separated from each other with reference to the through-hole blocking structure 422. This arrangement corresponds to the arrangement of the first receiving portion 411 and the second receiving portion 415 of the main body 410.

When the cover 420 is coupled to the main body 410, the first coupling portion 421 and the second coupling portion 425 may be simultaneously coupled to the first and second receiving portions 411, 415 of the main body 410. Alternatively, when the cover 420 is coupled to the main body 410, the first coupling portion 421 disposed at the lower portion of the cover inner surface 420a is first coupled to the main body 410 and then the second coupling portion 425 disposed at the upper portion of the cover inner surface 420a is coupled to the main body. Separation of the cover 420 from the main body 410 is performed in a reverse way to coupling therebetween by lifting the cover 420 upwards, followed by pulling the cover 420 in the forward direction. Specifically, when the cover 420 is lifted upwards, the first and second coupling portions 421, 425 are raised upwards along the first and second guide portions 411b, 415b of the first and second receiving portions 411, 415 and separated from the first and second catch portions 411c, 415c of the first and second receiving portions 411, 415, respectively. Then, when the cover 420 is pulled in the forward direction, the first and second coupling portions 421, 425 escape in the front direction of the main body 410 along the first and second guide portions 411b, 415b of the first and second receiving portions 411, 415.

It should be understood that coupling between the cover 420 and the main body 410 is not limited to the embodiments described with reference to FIG. 38 to FIG. 42. For example, the number of first coupling means and second coupling means is not limited to those shown in FIG. 38 to FIG. 42 and may be modified in various ways without departing from the object of the present disclosure. In addition, the arrangement of the first coupling means and the second coupling means is not limited to that shown in FIG. 38 to FIG. 42 and may be modified in various ways without departing from the object of the present disclosure. For example, the first coupling portion 421 and the first receiving portion 411 may be disposed at the upper sides of the cover 420 and the main body 410, and the second coupling portion 425 and the second receiving portion 415 may be disposed at the lower sides of the cover 420 and the main body 410.

Furthermore, although both the first coupling means and the second coupling means are used for coupling between the main body 410 and the cover 420 in FIG. 38, it should be understood that the present disclosure is not limited thereto. That is, the main body 410 may be coupled to the cover 420 only through the first coupling means using the latch mechanism. Alternatively, the main body 410 may be coupled to the cover 420 through the latch mechanism and the second coupling means including an additional coupling mechanism such as magnetic force, frictional force, bonding force, and the like.

In order to prevent loss of the cover 420 after separation of the cover 420 from the main body 410, an adhesive-type insect trap 1300 may further include at least one fastening member 430. Referring to FIG. 38, two fastening members 430 are connected to the main body 410 and the cover 420, respectively. The fastening members 430 prevent the cover 420 from being separated from the main body 410 by a predetermined distance or more. The kind of fastening member 430 is not particularly limited. For example, the fastening member 430 may include a ring, a chain or a string formed of a stretchable material.

It is apparent that the method of coupling the cover 420 to the main body 410 shown in FIG. 38 to FIG. 44 may be applied to the embodiments shown in FIG. 1 to FIG. 31.

Preparative Example: Preparation of Light Refractive Film

Light refractive films having different total light transmittances and haze values were prepared to evaluate fly trapping efficiency depending upon total light transmittance and haze of light refractive films applied to the adhesive-type insect traps according to the present disclosure.

TABLE 1

| Type | Specification | total light transmittance (%) | Haze (%) | Total light transmittance − Haze (%) |
|---|---|---|---|---|
| Tr. 1 | Kimoto Light-Up 50UK2 | 90.0 | 29.0 | 61 |
| Tr. 2 | Shinhwa Intertek SDC 746 | 96.91 | 93.84 | 3.07 |
| Tr. 3 | SkyLux CH153-D | 97.16 | 92.59 | 4.57 |
| Tr. 4 | Kimoto Light-Up 100UK4 | 90.6 | 46.0 | 44.6 |

Total light transmittance (%): Total light transmittance was measured at a visible light wavelength of 380 nm to 780 nm using a total light transmittance measurement instrument (NDH-7000, Nippon Denshoku Industries Co., Ltd.).

Haze (%): Haze was measured using a haze meter (NDH-7000, Nippon Denshoku Industries Co., Ltd.).

Example: Measurement of Fly Trapping Efficiency

Fly trapping efficiency of the adhesive-type insect traps 1000, 2000, 3000, 4000, 5000, 6000, 7000, 8000, 9000, 1100, 1200 provided with the light refractive films Tr. 1 to Tr. 3 prepared in Preparative Example were measured under the following conditions.

Standard for trapping test: closed space of 3.6 m×1.8 m×1.8 m

Installation height of adhesive-type insect trap: 150 cm

Irradiation time: 0.5 hours, 1 hour, 2 hours

Specification of light source: Two tube-type LED devices (2 bar) each provided with 10 LEDs emitting light having a wavelength of 365 nm Kind of fly: Housefly Temperature: 25.5° C.

Humidity: 66.0%

Experimental Example: Measurement Result of Fly Trapping Efficiency

Fly trapping efficiency of the adhesive-type insect traps prepared in Example are shown in Table 2.

TABLE 2

| | Time (hour) | | |
|---|---|---|---|
| Type | 0.5 | 1 | 2 |
| Tr. 1 | 65.5 | 90.3 | 97 |
| Tr. 2 | 94.4 | 98.2 | 100 |
| Tr. 3 | 89.1 | 95.7 | 98.5 |

As shown in Table 2, since all of Tr. 1 to Tr. 3 provided a trapping rate of 90% or more 1 hour after installation, it could be ascertained that the adhesive-type insect traps according to the present disclosure including the light refractive films had very high trapping rates.

In addition, Tr. 2 and Tr. 3 having a haze value of 30% or more provided a trapping rate of 80% or more 30 minutes after installation. Thus, it could be ascertained that the light refractive films having a haze value of 30% or more could generate refracted light providing significantly improved fly trapping efficiency.

Further, for Tr. 2 and Tr. 3 having a difference of less than 40% between total light transmittance and haze provided a trapping rate exceeding 89% 30 minutes after installation. That is, it could be ascertained that, when both total light transmittance and haze of a light refractive film were high or when a difference therebetween was not significant, a reaching distance of light having a high degree of refraction was increased, thereby significantly improving fly trapping efficiency.

In accordance with one aspect of the present disclosure, an adhesive-type insect trap includes: a main body having an adhesive sheet insertion hole; a light source mount disposed on the main body; and a cover detachably attached to the main body and having a through-hole formed in at least a portion thereof, wherein the adhesive sheet includes a flypaper piece and a sheet, the main body includes a guide unit guiding the adhesive sheet, and the cover includes a light refracting portion formed on an outer surface thereof or an inner surface thereof.

In accordance with another aspect of the present disclosure, an adhesive-type insect trap includes: a main body having an adhesive sheet insertion hole; a light source mount disposed on the main body; and a cover detachably attached to the main body and having a through-hole formed in at least a portion thereof, wherein the adhesive sheet includes a flypaper piece and a sheet, the main body includes a guide unit guiding the adhesive sheet, the cover includes at least one first coupling portion formed on an inner surface thereof, and the main body includes at least one first receiving portion formed on a front surface thereof such that the at least one first coupling portion is coupled to the first receiving portion when the cover is coupled to the main body.

An adhesive-type insect trap according to embodiments of the present disclosure can prevent the interior of the insect trap, particularly, insects collected therein, from being visibly observed from the outside while securing high insect trapping efficiency.

In addition, the adhesive-type insect trap according to the embodiments of the present disclosure may include an adhesive sheet secured to a main body thereof, thereby preventing the adhesive sheet having insects collected thereon from being easily separated from the main body.

Further, the adhesive-type insect trap according to the embodiments of the present disclosure allows light emitted from a light source thereof to be refracted or spread, thereby improving insect attraction efficiency with decoy light.

Further, the adhesive-type insect trap according to the embodiments of the present disclosure may emit UV light to attract insects and may generate carbon dioxide, thereby further improving an insect attraction effect.

Further, the adhesive-type insect trap according to the embodiments of the present disclosure has a deodorization effect, thereby providing a pleasant environment around the adhesive-type insect trap.

Further, the adhesive-type insect trap according to the embodiments of the present disclosure may include a light source for sterilization, thereby enabling killing of insects or sterilization of bacteria in insects trapped on the adhesive sheet within the insect trap.

Further, the adhesive-type insect trap according to the embodiments of the present disclosure may include a camera or a sensor to allow a user to monitor the kind of insect trapped on the adhesive sheet or to determine a time for replacement of the adhesive sheet, may have an alarm function to inform a user of the time for replacement of the adhesive sheet, thereby improving user convenience, and may automatically or manually control the intensity of light emitted from a light source depending upon the quantity of light around the adhesive-type insect trap, thereby enabling economically feasible power consumption and extension of lifespan of the light source while improving insect attraction efficiency with decoy light.

Further, the adhesive-type insect trap according to the embodiments of the present disclosure may include an insect attractant spray or an adhesive sheet containing an insect attractant, thereby improving insect attraction efficiency. Further, the adhesive-type insect trap according to the embodiments of the present disclosure may include a cover enabling easy coupling and separation while imparting high coupling force when the cover is coupled to a main body. Further, the adhesive-type insect trap according to the embodiments of the present disclosure may include a separable cover and can prevent loss of the cover separated from a main body.

Although some embodiments have been described herein, it should be understood that these embodiments are provided for illustration only and are not to be construed in any way as limiting the present disclosure, and that the scope of the present disclosure should be defined by the appended claims and equivalents thereof.

The invention claimed is:

1. An adhesive-type insect trap comprising:
a main body having an adhesive sheet insertion hole in which an adhesive sheet is inserted;
a plurality of light emitting sources configured to emit light having a wavelength range that attracts insects;
a light source mount disposed on the main body and mounting the plurality of light emitting sources thereon; and
a cover having an inner surface detachably attached to the main body and an outer surface opposite to the inner surface, the cover including a first transparent material and further having:
a through-hole formed in at least a portion thereof; and
a through-hole blocking structure configured to block at least a portion of the through-hole and extend from the cover to protrude outward from the cover;
wherein the adhesive sheet comprises a flypaper piece and a sheet,
the main body comprises a guide unit guiding the adhesive sheet, and
the cover comprises a light refracting portion formed on the outer surface or the inner surface of the cover; and
wherein the light refracting portion has a haze value of 30% or more, and
wherein the light refraction portion includes a roughness portion formed on the outer surface of the cover to refract light emitted from the plurality of light emitting sources, and
wherein the roughness portion includes a base attached to the outer surface of the cover and including a second transparent material same as the first transparent material and protrusions protruding from the base.

2. The adhesive-type insect trap according to claim 1, wherein the protrusions of the roughness portion comprise a first protrusion and a second protrusion attached to the first protrusion, the first protrusion and the second protrusion having different volumes.

3. The adhesive-type insect trap according to claim 1, wherein the light refracting portion has a total light transmittance value, and a difference between the total light transmittance value and the haze value is less than 40%.

4. The adhesive-type insect trap according to claim 1:
wherein the cover comprises at least one first coupling portion formed on the inner surface thereof,
a front surface of the main body comprises at least one first receiving portion, and
the at least one first coupling portion is coupled to the at least one first receiving portion when the cover is coupled to the main body.

5. The adhesive-type insect trap according to claim 4, wherein the at least one first coupling portion comprises a first support portion and a first hook portion, the at least one first receiving portion comprises a first guide portion and a first catch portion, and the first hook portion is caught by the first catch portion when the cover is coupled to the main body.

6. The adhesive-type insect trap according to claim 5, wherein the first hook portion is bent towards the inner surface of the cover and comprises a distal end having a greater thickness than other portions of the first hook portion.

7. The adhesive-type insect trap according to claim 5, wherein the first support portion comprises first assistant support portions protruding from the first support portion and adjoining the inner surface of the cover.

8. The adhesive-type insect trap according to claim 4, wherein the inner surface of the cover further comprises at least one second coupling portion, the front surface of the main body comprises at least one second receiving portion, and the at least one second coupling portion is coupled to the at least one second receiving portion when the cover is coupled to the main body.

9. The adhesive-type insect trap according to claim 8, wherein the at least one second coupling portion comprises a second support portion and a second hook portion, the at least one second receiving portion comprises a second guide portion and a second catch portion, and the second hook portion is caught by the second catch portion when the cover is coupled to the main body.

10. The adhesive-type insect trap according to claim 9, wherein the second hook portion further comprises a magnet member, the at least one second receiving portion further comprises a magnetic coupling portion, and the magnet member is coupled to the magnetic coupling portion by magnetic force when the cover is coupled to the main body.

11. The adhesive-type insect trap according to claim 4, further comprising: a light source for sterilization.

* * * * *